United States Patent
Freed et al.

(10) Patent No.: US 10,605,951 B2
(45) Date of Patent: Mar. 31, 2020

(54) METHOD OF DETERMINING CEC AND OTHER PROPERTIES FROM MULTI-FREQUENCY DIELECTRIC MEASUREMENTS

(71) Applicant: SCHLUMBERGER TECHNOLOGY CORPORATION, Sugar Land, TX (US)

(72) Inventors: Denise E. Freed, Newton Highlands, MA (US); Nikita V. Seleznev, Cambridge, MA (US); Chang-Yu Hou, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 486 days.

(21) Appl. No.: 14/875,077

(22) Filed: Oct. 5, 2015

(65) Prior Publication Data

US 2016/0097876 A1    Apr. 7, 2016

Related U.S. Application Data

(60) Provisional application No. 62/059,204, filed on Oct. 3, 2014.

(51) Int. Cl.
*G01V 3/38* (2006.01)
*G01V 3/24* (2006.01)
(Continued)

(52) U.S. Cl.
CPC ............... *G01V 3/38* (2013.01); *G01V 3/24* (2013.01); *G01V 3/30* (2013.01); *G01N 33/241* (2013.01);
(Continued)

(58) Field of Classification Search
CPC ... G01V 3/38; G01V 3/30; G01V 3/24; G01V 3/26; G01V 3/28; G01N 33/241;
(Continued)

(56) References Cited

U.S. PATENT DOCUMENTS

| | | | | |
|---|---|---|---|---|
| 4,703,277 A | * | 10/1987 | Kenyon | G01V 3/38 324/323 |
| 5,869,968 A | * | 2/1999 | Brooks | G01V 3/30 324/338 |

(Continued)

OTHER PUBLICATIONS

L. de Lima et al. "A generalized Maxwell-Wagner theory for membrane polarization in shaly sands." Geophysics, vol. 57, No. 3 (1992) [retrieved on Nov. 21, 2017]. Retrieved from STIC.*
(Continued)

*Primary Examiner* — Rehana Perveen
*Assistant Examiner* — Alfred H B Wechselberger

(57) ABSTRACT

Techniques involve inverting a dielectric dispersion model based on the geometrical and electrochemical effects that affect dielectric dispersion in fluid-saturated rocks and other porous formation with formation data and measurements to obtain further formation characteristics. A workflow involves using multi-frequency dielectric measurements of the dielectric constant and the conductivity of the formation for reservoir evaluation. The workflow also involves determining formation data such as matrix permittivity, formation temperature, pressure, and porosity, etc., and inverting the formation data and the multi-frequency dielectric measurements with the dielectric dispersion model to determine formation characteristics such as volumetric fraction of water in the formation, the formation water salinity and the Cation Exchange Capacity (CEC), etc. From the CEC log, in combination with other measurements, clay typing may be performed and swelling clays may be identified.

22 Claims, 16 Drawing Sheets

(51) Int. Cl.
G01V 3/30 (2006.01)
G06F 17/50 (2006.01)
G01N 33/24 (2006.01)
G01V 3/26 (2006.01)
G01N 33/28 (2006.01)

(52) U.S. Cl.
CPC ............ *G01N 33/2823* (2013.01); *G01V 3/26* (2013.01); *G06F 17/5009* (2013.01); *G06F 2217/16* (2013.01)

(58) Field of Classification Search
CPC ............ G01N 33/2823; G06F 17/5009; G06F 2217/16; G06F 15/5009; H04J 1/02
See application file for complete search history.

(56) References Cited

U.S. PATENT DOCUMENTS

| | | | | |
|---|---|---|---|---|
| 7,363,160 | B2* | 4/2008 | Seleznev | G01V 3/26 702/13 |
| 7,376,514 | B2* | 5/2008 | Habashy | G01V 3/26 702/13 |
| 7,863,901 | B2* | 1/2011 | Seleznev | G01V 3/12 324/335 |
| 2008/0215242 | A1* | 9/2008 | Ramakrishnan | A61B 17/0057 702/7 |
| 2008/0290874 | A1* | 11/2008 | Seleznev | G01V 3/12 324/337 |
| 2010/0283486 | A1* | 11/2010 | Comparon | G01V 3/30 324/686 |

OTHER PUBLICATIONS

Carmona et al. "Zapping Rocks." Oilfield Review, vol. 23, No. 1 (2011): Schlumberger [retrieved on Nov. 20, 2017]. Retrieved from <https://www.slb.com/~/media/Files/resources/oilfield_review/ors11/spr11/zapping_rocks.pdf>.*
Jones et al. "Surface area, geometrical and configurational effects on permittivity of porous media." Journal of Non-Crystalline Solids, vol. 305 (2002) [retrieved on Nov. 21, 2017]. Retrieved from <http://www.sciencedirect.com/science/article/pii/S0022309302010980>.*
Baker et al. "EPT Interpretation Using a Textural Model." SPWLA 26th Annual Logging Symposium (1985) [retrieved on Nov. 24, 2017]. Retrieved from STIC.*
Chew et al. "Dielectric enhancement due to electrochemical double layer: Thin double layer approximation." Journal of Chemical Physics, vol. 77, No. 9 (1982) [retrieved on Nov. 17, 2017]. Retrieved from <http://aip.scitation.org/doi/abs/10.1063/1.444369>.*
Garrouch et al. "An Inverted Petrophysical Model for Shaly Sands." In Situ, vol. 19, No. 2 (1995) [retrieved on Nov. 20, 2017]. Retrieved from STIC.*
Tyc et al. "Geometrical models for the high-frequency dielectric properties of brine saturated sandstones." Journal of Applied Physics, vol. 64, No. 5 (1988) [retrieved on Nov. 20, 2017]. Retrieved from <http://aip.scitation.org/doi/abs/10.1063/1.341645>.*
Seleznev, et al. "Formation Properties Derived from a Multifrequency Dielectric Measurement." SPWLA 47th Annual Logging Symposium (2006) [retrieved on Nov. 20, 2017]. Retrieved from STIC.*
Chassagne et al. "The dielectric response of a colloidal spheroid." Journal of Colloid and Interface Science, vol. 326 (2008) [retrieved on Nov. 21, 2017]. Retrieved from <http://www.sciencedirect.com/science/article/pii/S0021979708007984>.*
Norris et al. "A Generalized Differential Effective Medium Theory." Journal of Mechanics and Physics of Solids, vol. 3, No. 6 (1985) [retrieved on Nov. 22, 2017]. Retrieved from <http://www.sciencedirect.com/science/article/pii/0022509685900018?via%3Dihub>.*

Namdar-Khojasteh, et al. "Estimating Soil Water Content from Permittivity for Different Minerologies and Bulk Densities." Soil Science Society of America Journal, vol. 76 (2011) [retrieved on Nov. 17, 2017]. Retrieved from <https://dl.sciencesocieties.org/publications/sssaj/abstracts/76/4/1149>.*
Bean et al. "New Wireline Dielectric Dispersion Logging Tool Result in Fluvio-Deltaic Sands Drilled with Oil-Based Mud." SPWLA 54th Annual Logging Symposium (Jun. 2013) [retrieved on Nov. 20, 2017]. Retrieved from <http://www.slb.com/~/media/Files/technical_papers/2013/spwla_2013_dielectric_scanner.pdf>.*
Garrouch et al. "A classification model for rock typing using dielectric permittivity and petrophysical data." Journal of Geophysical Prospecting, vol. 6 (2009) [retrieved on Nov. 17, 2017]. Retreived from <http://iopscience.iop.org/article/10.1088/1742-2132/6/3/010/meta>.*
Wikipedia contributors. "Double layer (surface science)." Wikipedia, The Free Encyclopedia (Jul. 1, 2018) [retrieved on Jul. 20, 2018]. Retrieved from <https://en.wikipedia.org/wiki/Double_layer_(surface_science)#Stern> (Year: 2018).*
Sen et al. "Dielectric Enhancement due to geometrical and electrochemical effects" AIP Conference Proceedings No. 107: American Institute of Physics (1984) [retrieved on Nov. 28, 2017]. Retrieved from STIC. (Year: 1984).*
Birchak et al., "High Dielectric Constant Microwave Probes for Sensing Soil Moisture", Proceedings of the IEEE, vol. 62, No. 1, Jan. 1974, pp. 93-98.
Boyarskii et al., "Model of dielectric constant of bound water in soil for applications of microwave remote sensing", Progress in Electromagnetics Research, PIER 35, 2002, pp. 251-269.
Chassagne et al., "The dielectric response of a colloidal spheroid", Journal of Colloid and Interface Science, vol. 326, 2008, pp. 240-253.
Chew, "Dielectric enhancement and electrophoresis due to an electrochemical double layer: A uniform approximation", The Journal of Chemical Physics, vol. 80, No. 9, May 1984, pp. 4541-4552.
Chew et al., "Dielectric enhancement due to electrochemical double layer: Thin double layer approximation", The Journal of Chemical Physics, vol. 77, No. 9, Nov. 1982, pp. 4683-4693.
Clavier et al., "Theoretical and Experimental Bases for the Dual-Water Model for Interpretation of Shaly Sands", Society of Petroleum Engineers Journal, Apr. 1984, pp. 153-168.
De Lima et al., "A generalized Maxwell-Wagner theory for membrane polarization in shaly sands", Geophysics, vol. 57, No. 3, Mar. 1992, pp. 431-440.
Fixman, "Charged macromolecules in external fields. I. The sphere", The Journal of Chemical Physics, vol. 72, No. 9, May 1980, pp. 5177-5186.
Fixman, "Thin double layer approximation for electrophoresis and dielectric response", The Journal of Chemical Physics, vol. 78, No. 3, Feb. 1983, pp. 1483-1491.
Goode et al., "Charge density and permeability in clay-bearing sandstones", Geophysics, vol. 53, No. 12, Dec. 1988, pp. 1610-1612.
Grau et al., "A Geological Model for Gamma-ray Spectroscopy Logging Measurements", Nuclear Geophysics, vol. 3, No. 4, 1989, pp. 351-359.
Grau et al., "Elemental Concentrations from Thermal Neutron Capture Gamma-ray Spectra in Geological Formations", Nuclear Geophysics, vol. 3, No. 1, 1989, pp. 1-9.
Han et al., "Continous Estimate of Cation Exchange Capacity from Log Data: A New Approach Based on Dielectric Dispersion Analysis", SPWLA 53rd Annual Logging Symposium, Jun. 16-20, 2012, pp. 1-15.
Herron, "Estimating the Intrinsic Permeability of Clastic Sediments from Geochemical Data", SPWLA Twenty-Eighth Annual Logging Symposium, Jun. 29-Jul. 2, 1987, pp. 1-23.
Hinch et al., "Dielectric Response of a Dilute Suspension of Spheres with Thin Double Layers in an Asymmetric Electrolyte", Journal of the Chemical Society, Faraday Transactions 2, vol. 80, pp. 535-551.
Hizem et al., "Dielectric Dispersion: A New Wireline Petrophysical Measurement", SPE 116130 presented at the 2008 Annual Technical Conference and Exhibition held in Denver, Colorado, USA, Sep. 21-24, 2008, pp. 1-21.

(56) References Cited

OTHER PUBLICATIONS

Klein et al., "An Improved Model for the Dielectric Constant of Sea Water at Microwave Frequencies", IEEE Transactions on Antennas and Propagation, vol. AP-25, No. 1, Jan. 1977, pp. 104-111.

O'Konski, "Electric Properties of Macromolecules v. Theory of Ionic Polarization in Polyelectrolytes", The Journal of Physical Chemistry, vol. 64, May 1960, pp. 605-619.

Patchett, "An Investigation of Shale Conductivity", SPWLA Sixteenth Annual Logging Symposium, Jun. 4-7, 1975, pp. 1-41.

Polder et al., "The Effective Permeability of Mixtures of Solids", Physica XII, No. 5, Aug. 1946, pp. 257-271.

Raythatha et al., "Dielectric Properties of Clay Suspensions in MHz to GHz Range", Journal of Colloid and Interface Science, vol. 109, No. 2, Feb. 1986, pp. 301-309.

Schurr, "On the Theory of the Dielectric Dispersion of Spherical Colloidal Particles in Electrolyte Solution", The Journal of Physical Chemistry, vol. 68, No. 9, Sep. 1964, pp. 2407-2413.

Schwarz, "A Theory of the Low-frequency Dielectric Dispersion of Colloidal Particles in Electrolyte Solution", The Journal of Physical Chemistry, vol. 66, Dec. 1962, pp. 2636-2642.

Seleznev et al., "Formation Properties Derived from a Multi-frequency Dielectric Measurement", SPWLA 47th Annual Logging Symposium, Jun. 4-7, 2006, pp. 1-12.

Sen et al., "A self-similar model for sedimentary rocks with application to the dielectric constant of fused glass beads", Geophysics, vol. 46, No. 5, May 1981, pp. 781-795.

Sen et al., "Electrical conduction in clay bearing sandstones at low and high salinities", Journal of Applied Physics, vol. 63, No. 10, May 1988, pp. 4832-4840.

Sen et al., "Surface-to-volume ratio, charge density, nuclear magnetic relaxation, and permeability in clay-bearing sandstones", Geophysics, vol. 55, No. 1, Jan. 1990, pp. 61-69.

Sihvola et al., "Polarizability and Effective Permittivity of Layered and Continuously Inhomogeneous Dielectric Ellipsoids", Journal of Electromagnetic Waves and Applications, vol. 4, No. 1, 1990, pp. 1-26.

Stroud et al., "Analytical model for the dielectric response of brine-saturated rocks", Physical Review B, vol. 34, No. 8, Oct. 1986, pp. 5145-5153.

Vinegar et al., "Induced polarization of shaly sands", Geophysics, vol. 49, No. 8, Aug. 1984, pp. 1267-1287.

Waxman et al., "Electrical Conductivities in Oil-Bearing Shaly Sands", Society of Petroleum Engineers Journal, Jun. 1968, pp. 107-122.

\* cited by examiner

FIG. 10
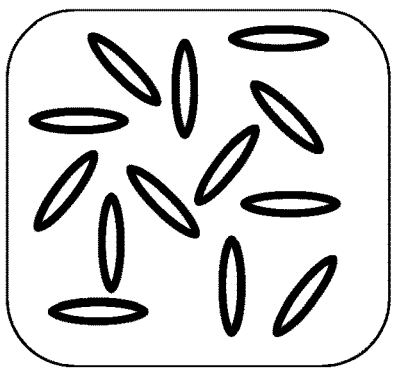
Mineral Matrix + Water Phase = Background Phase
Geometric dispersion model used for mixing
Mineral matrix grain are generally spheroidal
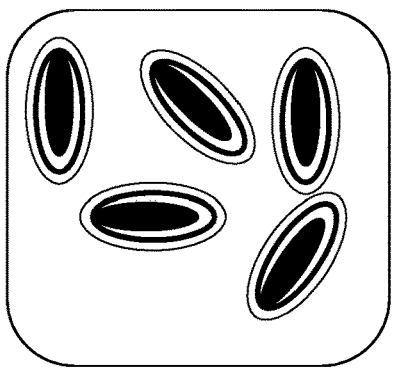
Background Phase + Clay Particles = Dielectric Dispersion of Shaly Sand Rock
Maxwell-Garnett Law or other model used for mixing.
Clay particles are spheroids coated with layer of bound water and EDL.
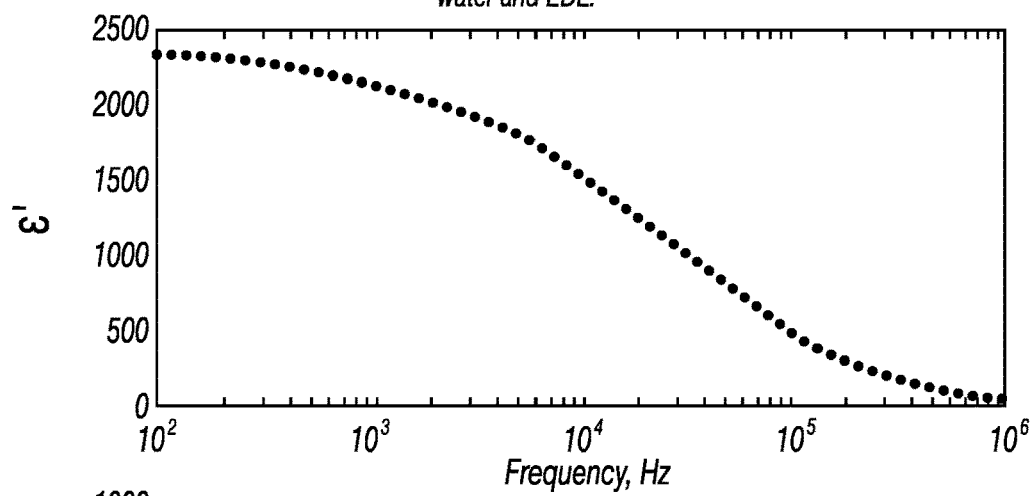
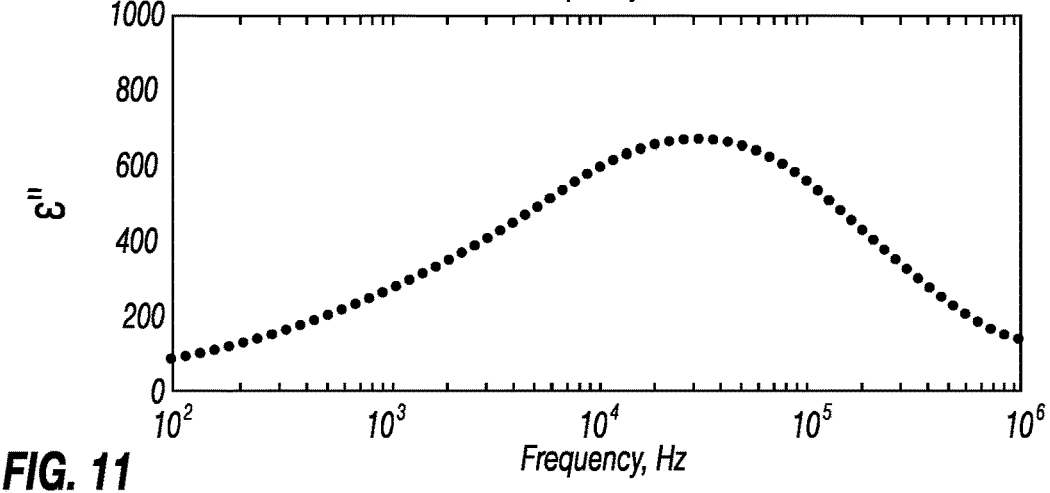
FIG. 11

METHOD OF DETERMINING CEC AND OTHER PROPERTIES FROM MULTI-FREQUENCY DIELECTRIC MEASUREMENTS

RELATED APPLICATIONS

This application claims the benefit of and priority to U.S. Provisional Patent Application 62/059,204, entitled "METHOD OF DETERMINING CEC AND OTHER PROPERTIES FROM MULTI-FREQUENCY DIELECTRIC MEASUREMENTS," filed Oct. 3, 2014.

BACKGROUND

The present invention relates to techniques for performing wellbore operations. More particularly, the present invention relates to techniques for determining characteristics of subterranean formations.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions.

Oil rigs are positioned at wellsites for performing a variety of oilfield operations, such as drilling a wellbore, performing downhole testing, and/or producing located hydrocarbons. To produce hydrocarbons economically, an accurate estimation of hydrocarbon volume may be performed. Conventional resistivity interpretation techniques may be less reliable in the presence of clays, which often increase formation conductivity and may mask the presence of hydrocarbons.

Several physical models have been developed to address the influence of clays on the physical properties of formations, and to accurately determine hydrocarbon volume from resistivity measurements. For example, the Waxman-Smits and Dual-Water models have been used in the oilfield industry. However, conventional models may be affected by various uncertainties and inaccuracies of what is known of the formation. For example, the Waxman-Smits model uses an external input of the formation Qv (the Cation Exchange Capacity per unit pore volume). However, the Cation Exchange Capacity (CEC) is often inferred from indirect formation lithology or lab measurements which may be affected by uncertainties in determination of the formation lithology and clay type. Alternative techniques of measuring the CEC in a lab uses well coring, which can be relatively time consuming.

SUMMARY

A summary of certain embodiments disclosed herein is set forth below. It should be understood that these aspects are presented merely to provide the reader with a brief summary of these certain embodiments and that these embodiments are not intended to limit the scope of the systems and methods described herein. Indeed, embodiments of systems and methods described herein may encompass a variety of aspects that may not be set forth below.

Embodiments described herein relate to systems, methods, and computer-readable media for determining formation properties based on multi-frequency dielectric measurements. According to some embodiments, a method is provided that includes obtaining multi-frequency dielectric measurements comprising dielectric measurements measured from a formation at a plurality of frequencies, inputting the multi-frequency dielectric measurements into a dispersion model, determining a Cation Exchange Capacity (CEC) of a formation from inputting the multi-frequency dielectric measurements in the dispersion model, and determining a characteristic related to a shape of clay in the formation from inputting the multi-frequency dielectric measurements in the dispersion model.

Additionally, in some embodiments, a method is provided for determining a Cation Exchange Capacity (CEC) of a formation. The method includes measuring multi-frequency dielectric measurements from the formation, wherein the multi-frequency dielectric measurements comprise dielectric measurements measured from the formation at a plurality of frequencies, using a dielectric dispersion model including both geometric and electrochemical effects of the formation and clay in the formation over the plurality of frequencies, and inputting the multi-frequency dielectric measurements along with one or more additional formation characteristics with the dielectric dispersion model to output the CEC of the formation.

Moreover, in some embodiments, a non-transitory computer-readable medium storing computer-executable instructions is provided. When executed by at least one processor, the instructions cause the at least one processor to perform the following: inputting multi-frequency dielectric measurements into a dielectric dispersion model, wherein the multi-frequency dielectric measurements comprise dielectric measurements obtained from a formation at a range of multiple frequencies, and wherein the dielectric dispersion model is based on geometric and electrochemical effects of the formation and clay in the formation over the range of multiple frequencies and inverting the multi-frequency dielectric measurements with the dielectric dispersion model to output a Cation Exchange Capacity (CEC) of the formation.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Additionally, depending on the context, singular and plural terminology may be used interchangeably.

FIG. 10 is a schematic representation of a general mixing scheme for a physics-based dielectric dispersion model of clay-containing rocks in accordance with one or more example embodiments.

FIG. 11 is a plot of a prediction of the double layer model in accordance with one or more example embodiments.

DETAILED DESCRIPTION

Figure 1:
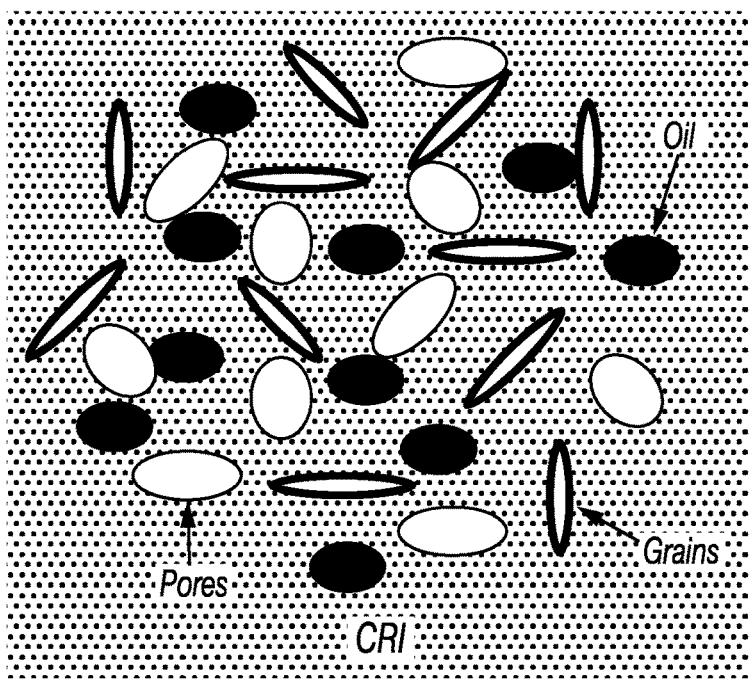
FIG. 1 is a graphical representation of a textural model in accordance with one or more example embodiments.

One or more specific embodiments of the present disclosure will be described below. These described embodiments are just examples of the presently disclosed techniques. Additionally, in an effort to provide a concise description of these embodiments, features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

The present techniques relate to dielectric logging of geological formations. One or more embodiments presented in this disclosure include methodologies for determining formation Cation Exchange Capacity (CEC), cation charge per unit pore volume (Qv), and other petrophysical parameters of interest from multi-frequency dielectric dispersion logging. Techniques involve combining geometrical, electrochemical, and bound water effects that describe the dielectric properties of earth formation in a wide frequency range. Moreover, embodiments describe the interpretation workflow that determines the volumetric fraction of water in the formation, the formation water salinity, and the CEC and/or Qv.

One or more embodiments of the present techniques relate to a workflow for combining geometrical and electrochemical effects that are responsible for the dielectric dispersion in fluid-saturated rocks and other porous media. The workflow involves using multi-frequency measurements of the dielectric constant and conductivity for reservoir evaluation. Some embodiments involve inverting the data and measurements of the combined geometrical and electrochemical effects and the multi-frequency measurements with a dispersion model to determine various outputs related to characteristics of the water and/or formation. For example, in some embodiments, the workflow(s) may involve determining the volumetric fraction of water in the formation, the formation water salinity, and the CEC, as well as other information which may be analyzed or determined based on the these outputs.

In accordance with the present techniques, determining the formation CEC and/or Qv in situ at downhole conditions as a continuous log may improve determination of the hydrocarbon content from resistivity logging. Combining or comparing the CEC log with other measurements may further enable clay typing, provide clay reactivity index for optimum non-reactive frac fluid design, and identify swelling clays. Identifying swelling clays may be important for developing an optimal reservoir completion strategy. The clay typing and the CEC may be related to the formation permeability.

In one or more embodiments, the workflow may involve receiving inputs or prior knowledge of the formation, such as local geology, rock type, rock fluids type, etc. The multi-frequency measurements of the formation dielectric constant and conductivity may also be input. Various other measurements may also be input into the workflow, including previously known parameters and future measurements made. Furthermore, the techniques may be applied to laboratory measurements on samples of rocks, clays, and fluids to determine their contents. The techniques may also have applications outside the oilfield industry for evaluation of complex composite materials, such as concrete or cement, as well as in other geophysical contexts, such as water resource evaluations and environmental spillage evaluations.

Figure 2:
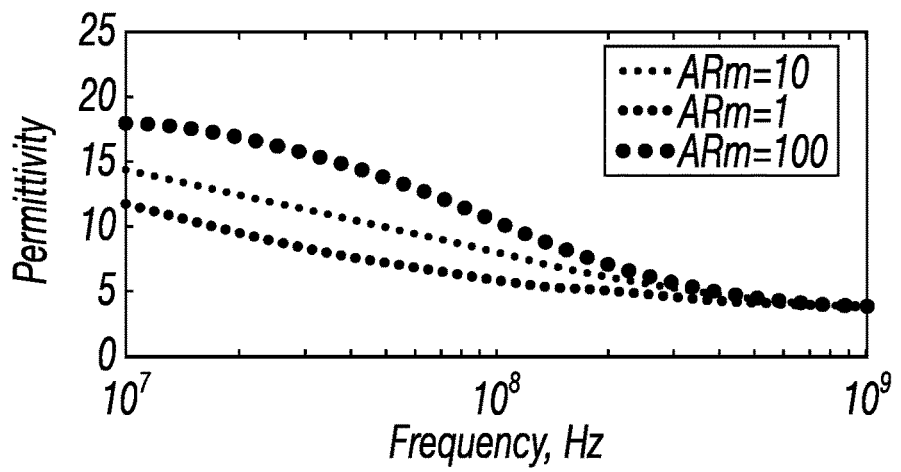
FIG. 2 includes plots showing the effect of variation of the grain aspect ratio in accordance with one or more example embodiments.
Figure 2:
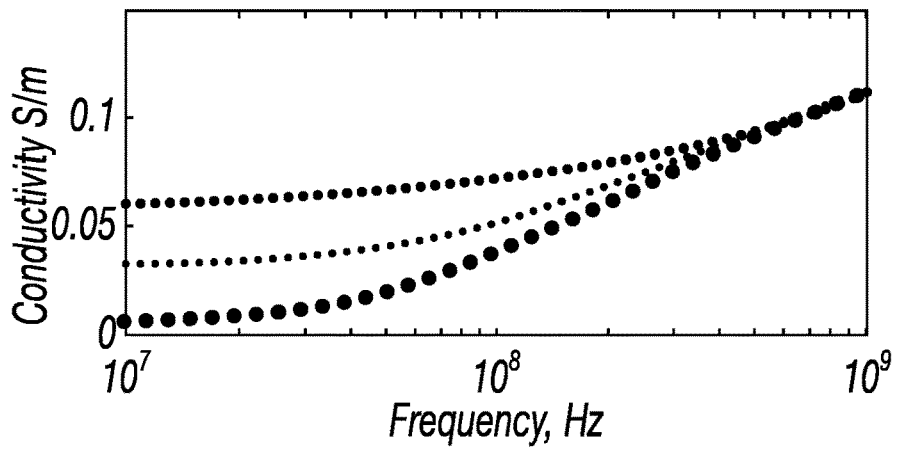

The textural model has conventionally been used for determining the dielectric effects due to the texture of a rock matrix. FIG. 1 is a graphical representation of the textural model 10, including pores 12, grains 14, and oil 16, and FIG. 2 are plots showing the effect of variation of the grain aspect ratio, where plot 20 represents plotlines 22, 24, and 26 having low, medium, and high aspect ratios respectively, in frequency with respect to permittivity. Plot 28 represents the plotlines 22', 24', and 26' having the same respective aspect ratios in frequency with respect to conductivity. A higher aspect ratio of the grains as in plotline 26 generally leads to a stronger dielectric and conductivity dispersion. At the same time, the high aspect ratio grains as in plotline 26 may have an effect of lowering the overall rock conductivity as they prevent flow of the electric current.

Figure 3:
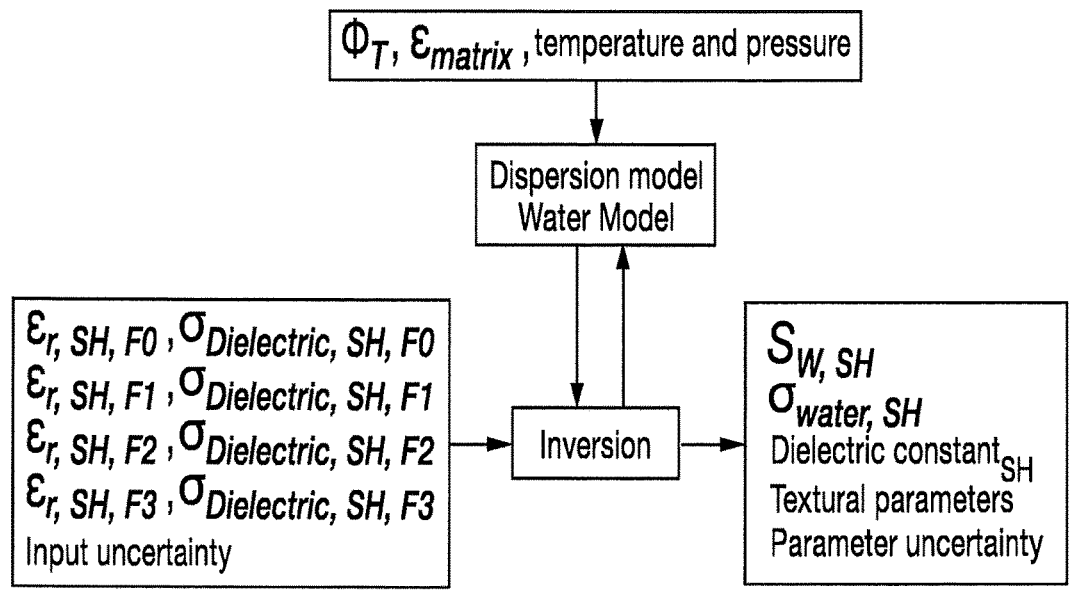
FIG. 3 is a representation of a workflow for determining the formation hydrocarbon content and water salinity from multi-frequency dielectric measurements in accordance with one or more example embodiments.

FIG. 3 is a representation of a conventional workflow 30 for determining the formation hydrocarbon content and water salinity from multi-frequency dielectric measurements. The analysis uses inputs 32 including the multi-frequency measurements of the formation dielectric constant and conductivity, the formation total porosity, the rock matrix dielectric constant, and the formation temperature and pressure. These data 32 may be inverted (block 34) with a model 36, such as a dielectric dispersion model and a water model, to produce outputs 38, including the formation hydrocarbon saturation, water salinity, and textural parameters (e.g., cementation exponent or aspect ratios of the constituent fractions). The high-frequency dielectric properties of water are computed using a water model having inputs 37 of water salinity, pressure, and temperature. Alternatively, the formation water-filled porosity may be estimated directly without the input of the total porosity assuming that only mineral matrix (including clay) and a water phase are present in the rock.

The dielectric dispersion properties of clay-containing formations, such as shaly sands, are more complex than those of clean formations due to the presence of the CEC and the bound water effects in addition to the textural effects. These additional effects, if not accounted for, may sometimes lead to the incorrect estimation of the hydrocarbon saturation or water-filed porosity in clay-containing formations. For example, a shaly sand model may take the clay effects into account by taking an empirical model for dielectric constant of water to include the effect of clays and combine the clay effect with a host rock whose properties are estimated using a physically allowed, but not unique model that disregards the grain structures. In addition, this empirical model may involve calibration on core data and may not be sufficiently robust to provide answers in all environments.

Figure 4:
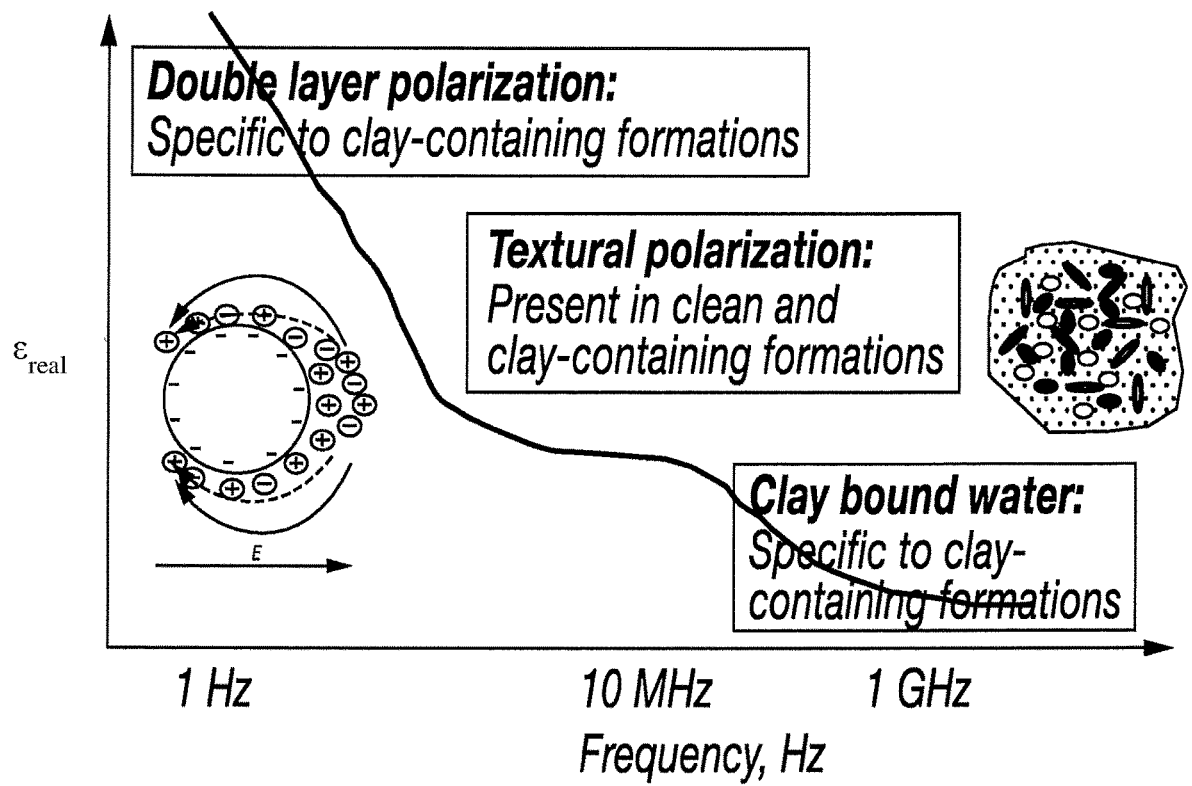
FIG. 4 is a schematic representation of multiple mechanisms defining dielectric properties of formations in accordance with one or more example embodiments.

In accordance with the present techniques, the workflow may be applied to a range of shaly sand environments. Dielectric response of shaly sands is governed by the response of the free water, interfacial polarization, electrochemical polarization of the electrical double layer (EDL), and dielectric properties of bound water. FIG. 4 is a schematic representation of multiple mechanisms defining dielectric properties of clay-containing formations. In some embodiments, the superposition of polarization and bound water effects contributes to the dielectric response in a wide frequency range including RF and microwave frequencies employed in the dielectric logging. The effect of rock texture on the host medium properties is an important contribution at higher-frequencies. Further, the geometric dispersion contribution from the clay phase may be considered by assigning textural parameters, such as clay particle shape. The mixing technique represents experimentally observed dielectric properties of clay-containing formations in MHz-GHz frequency range.

The interfacial polarization arises due to accumulation of charges on interfaces between regions with different conductivity, the effect sometimes referred to as the Maxwell-Wagner effect. In saturated rocks these interfaces are often the pore walls separating conductive brine and non-conductive mineral rock matrix or interfaces between brine and hydrocarbon phases. The effective medium models address interfacial polarization mechanisms and its dependence on rock texture in clay-free environments.

Rock-forming minerals such as quartz, carbonates and kaolinite have surfaces rich in oxygen atoms creating local fields of negative charge. These attract the protons of negatively charged hydroxyl ions [OH$^-$] in the brine making the mineral and the double layer negatively charged. Clay minerals, such as illite and montmorillonite, on the other hand, have a second source of surface charge. During their formation, these clays develop negative sites on their surface due to substitution inside the crystal structure and on the surface, for example magnesium [MG$^{2+}$] replacing aluminum [Al$^{3+}$]. These sites are then neutralized by cations such as Na$^+$, Ca$^{2+}$, Ba$^{2+}$ and NH$_4^+$, called counterions, that absorb on the clay's surface. The concentration of the counter ions is proportional to the CEC, the cation exchange capacity of the clays. Mixed with brine, these counterions dissociate from the clay and form a "double layer".

Figure 5:
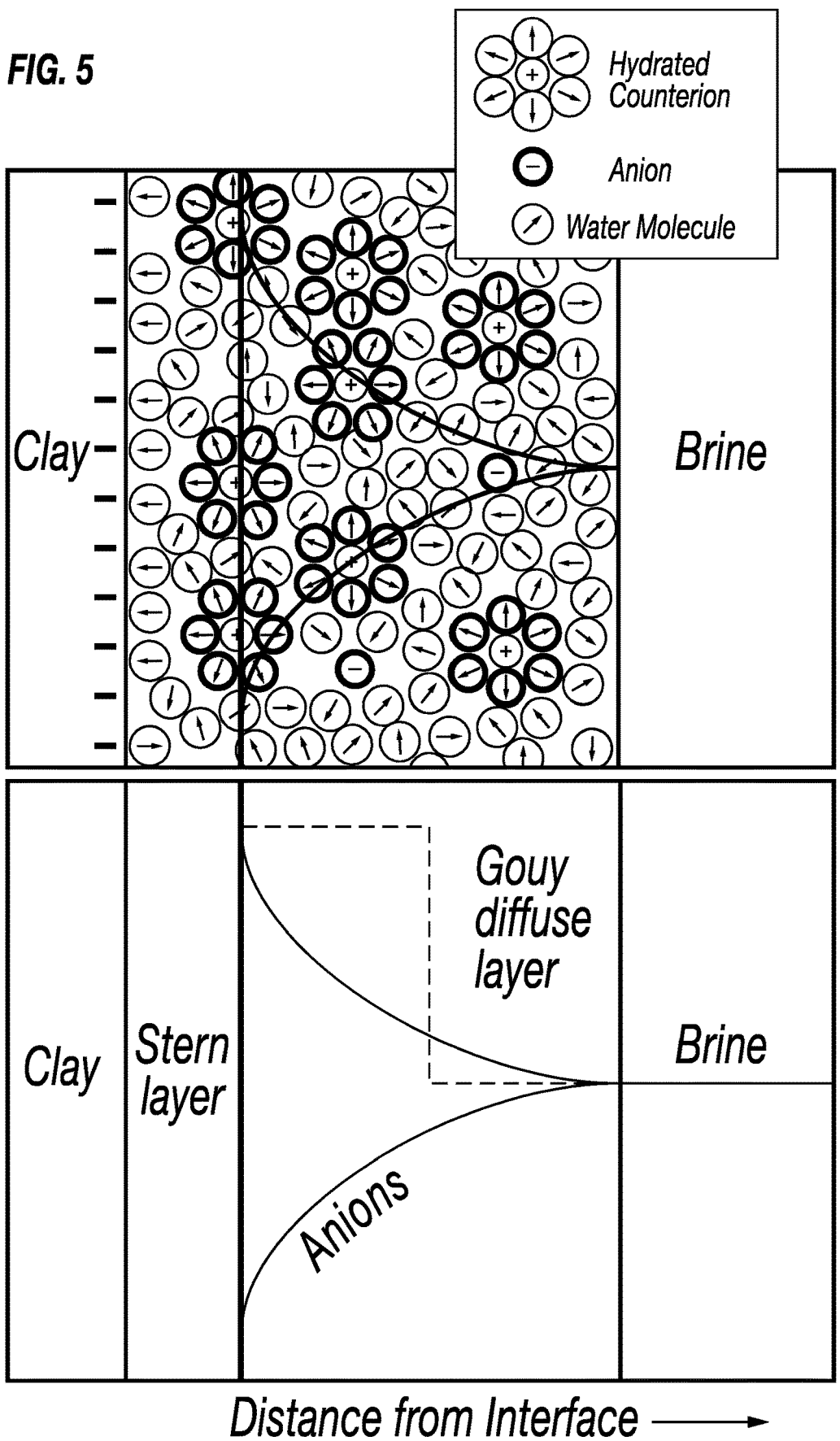
FIG. 5 is a schematic representation of the double layer in accordance with one or more example embodiments.

The double layer is schematically represented in FIG. 5. Some charges remain on the surface, forming the so-called Stern or fixed layer, while other cations reside in a diffuse cloud in which the cation concentration decreases to the level of that in the brine, as one moves away from the interface, forming the so-called Gouy-Chapman or diffuse layer. All the mobile counter ions are responsible for shaly sand conductivity and dielectric enhancement, and thus, the latter are proportional to CEC, the cation exchange capacity of the clays.

Figure 6:
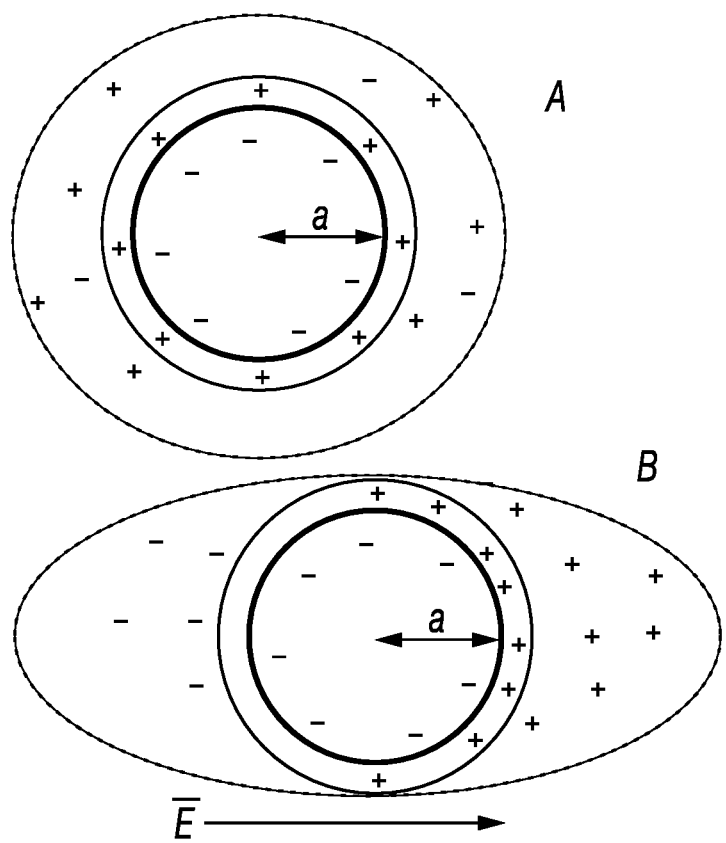
FIG. 6 is a schematic representation of the double layer polarization in the external field in accordance with one or more example embodiments.

Theoretical models ascribe large dielectric enhancements observed at lower frequencies to the polarization of the double layer also referred to as the electrochemical polarization. The schematic representation of the double layer polarization in the external field is shown in FIG. 6. The magnitude of the enhancement due to double layer is dependent on the frequency, brine salinity, and abundance of the double layer. The cation exchange capacity of clays is directly proportional to the specific surface area of most common clays: montmorillonite, illite and kaolinite. The double layer abundance may be directly proportional to the surface area where it is formed and thus may provide a quantitative link between the abundance of the double layer and the formation CEC. The electrochemical polarization effects are typically dominant at low frequencies and can lead to very large dielectric enhancements. In the presence of clays electrochemical effects are so significant that it still plays a role even at relatively high frequencies in the MHz-GHz range.

Embodiments of the present disclosure involve modeling shaly sands with multi-frequency dielectric measurements to determine the CEC of the formation. In one or more embodiments, a first model is based on the dielectric response of clay grains and a second model is based on the dielectric response of mixtures of clay grains with the rest of the rock matrix and brine. The clay grains are charged, which causes a double layer effect. Furthermore, the clay grains may have a platy shape, which both modifies the double-layer effect and contributes to textural effects. Embodiments include different schemes for mixing the grains with rock matrix and brine, and then including the dielectric response of the clay grains.

Mixing Laws

In some embodiments, a model for the rock with clay grains may use the fewest possible parameters while accounting for the relevant physics. Both the chemical and the shape effects may be modeled by taking the clay grains to be spheroids with surface charge. In one embodiment, to model the rock and to take into account the effect of mixing clay grains with the other rock grains, water, and hydrocarbons, the clay grains may be combined with rock grains and the fluid phases by using a differential effective medium model.

Figure 7:
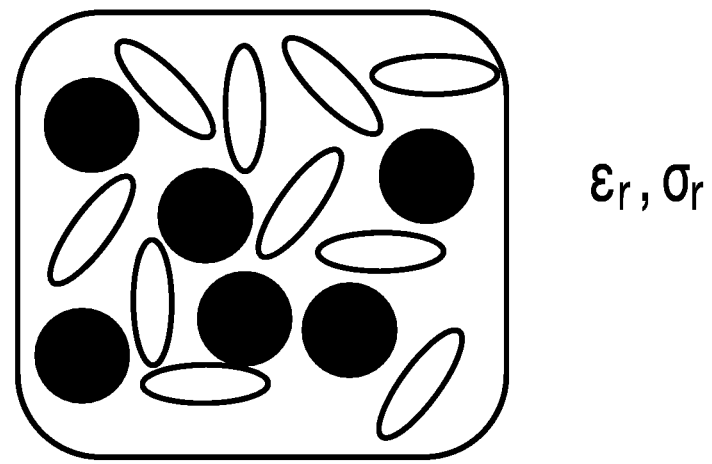
FIG. 7 is a schematic representing a general mixing scheme of rock grains, clay grains, and water in accordance with one or more example embodiments.

Because there is only a limited amount of information in the dielectric dispersion data, the model may be limited to as few parameters as possible. In one embodiment of the invention, it may be assumed that all the texture in the shaly sands comes from the clay grains. For example, as in the first model, the rock may be modeled as a collection of spherical, non-charged rock grains and spheroidal, charged clay grains with a fixed aspect ratio. A schematic of this model is shown in FIG. 7 which represents rock grains 32 and clay grains 34 in water 36. The model is based on the volume fraction of the clay grains, p, the aspect ratio of the clay grains, and the CEC of the clay grains. When the CEC is set to zero, this model reduces to the usual bimodal model, where p is the fraction of the platy grains and is related to Archie's exponent, or cementation exponent, m. For rocks with non-clay grains that are platy or have flat surfaces, all the texture may not necessarily come from the clay. However, for rocks consisting mainly of clay and quarts, this description may be adequate to describe the dielectric response. In other embodiments of the invention, additional spheroidal shapes can be included to represent the texture of the non-clay rock grains. In accordance with the present techniques, rock texture may refer to the cementation exponent of the formation or volume fractions and shape of the spheroids in the formation.

The first model may also be affected by whether the grains are randomly oriented or are aligned parallel or perpendicular to the electric field. In the model, it may be assumed that $f_{aligned}$ equals the fraction of grains whose axis of symmetry is aligned with the electric field. For oblate spheroids, the electric field may be perpendicular to the flat surface of the spheroid. When the spheroids are randomly oriented, $f_{aligned}=\frac{1}{3}$. In the model, it may further be aligned assumed that $f_{aligned}=\frac{1}{3}$ as the default, but if there is significant orientation of the grains, other values of this parameter will be more appropriate.

This mixing model is based on the CEC through the effective clay conductivities, $\sigma_p$ and $\sigma_n$. The effective clay conductivities $\sigma_n$ and $\sigma_p$ may be calculated from the CEC, as will be described in Equation (31). The complex permittivity of the clay grains may then be defined as $$\varepsilon_p = \varepsilon_c + i\frac{\sigma_p}{\omega\varepsilon_0}, \quad (1)$$

and $$\varepsilon_n = \varepsilon_c + i\frac{\sigma_n}{\omega\varepsilon_0}, \quad (2)$$

for the electric field parallel and perpendicular to the axis of symmetry, respectively. In equations (1) and (2), $\varepsilon_c$ is the dielectric permittivity of the dry clay. The permittivity of the rest of the dry rock matrix is given by $\varepsilon_m$. $\varepsilon_c$ and $\varepsilon_m$ may equal the average permittivity of the dry rock matrix with the clay.

To calculate the dielectric response for the model using the differential effective medium theory, some embodiments assume that the porosity of the rock is related to the complex permittivity of the water, given by $\varepsilon_w^* = \varepsilon_w + i\sigma_w/(\omega\varepsilon_0)$, and to the complex permittivity of the rock, given by $\varepsilon_r^* = \varepsilon_r + i\sigma_r/(\omega\varepsilon_0)$, as follows:

$$\phi = \prod_{i=0}^{3} \left(\frac{\varepsilon_w^* - r_i}{\varepsilon_r^* - r_i}\right)^{p_i}. \quad (3)$$

In equation (3), $r_0=0$, and $r_1$, $r_2$, and $r_3$ are the roots of the polynomial $N(\varepsilon)$ given by $$N(\varepsilon) = (1-p)(\varepsilon_m - \varepsilon)(d_L\varepsilon + (1-d_L)\varepsilon_p)((2-d_L)\varepsilon + d_L\varepsilon_n) + \quad (4)$$
$$\frac{p}{3}f_{aligned}(\varepsilon_p - \varepsilon)(2\varepsilon + \varepsilon_m)((2-d_L)\varepsilon + d_L\varepsilon_n) +$$
$$\frac{2p}{3}(1 - f_{aligned})(\varepsilon_n - \varepsilon)(2\varepsilon + \varepsilon_m)(d_L\varepsilon + (1-d_L)\varepsilon_p),$$

where $d_L = 1 - L$ and L is the depolarization factor along the axis of symmetry. It is given by $$L = -(1+\xi_0^2)(\xi_0 \tan^{-1}(1/\xi_0) - 1). \quad (5)$$

where the spheroidal coordinate $\xi_0$ is related to the aspect ration, b/a, where a is half the major axis and b is half the minor axis of the spheroid. It is given by $$\xi_0 = \frac{(b/a)^2}{(1-(b/a)^2)}. \quad (6)$$

In equation (3), the exponents $p_i$ are the residues of the rational function $D(\varepsilon)/(3\varepsilon N(\varepsilon))$ where $D(\varepsilon)$ is given by $$D(\varepsilon) = (2\varepsilon + \varepsilon_m)(d_L\varepsilon + (1-d_L)\varepsilon_p)((2-d_L)\varepsilon + d_L\varepsilon_n) \quad (7)$$

In accordance with the present techniques, this mixing law or one of the other mixing laws described below can be used to combine the rock grains, clay grains and water in the rock. The resulting model can the be fit to dielectric data to determine the water-filled porosity, the water salinity, the CEC, the aspect ratio of the clay or the cementation exponent, and the low-frequency resistivity.

Figure 8:
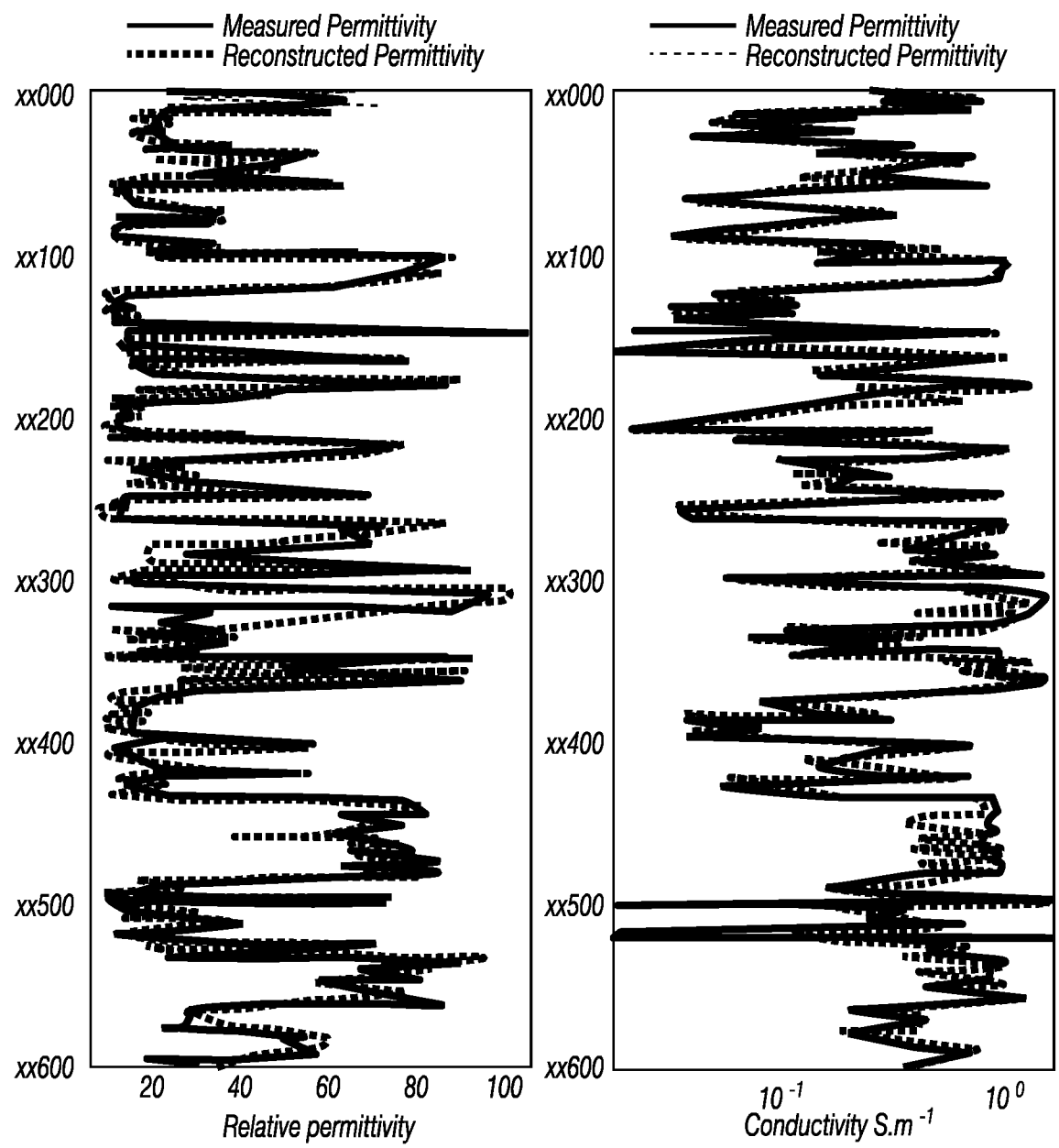
FIG. 8 represents a model-fitted permittivity and conductivity compared to measured data from a log of a shaly sand in accordance with one or more example embodiments.
Figure 9:
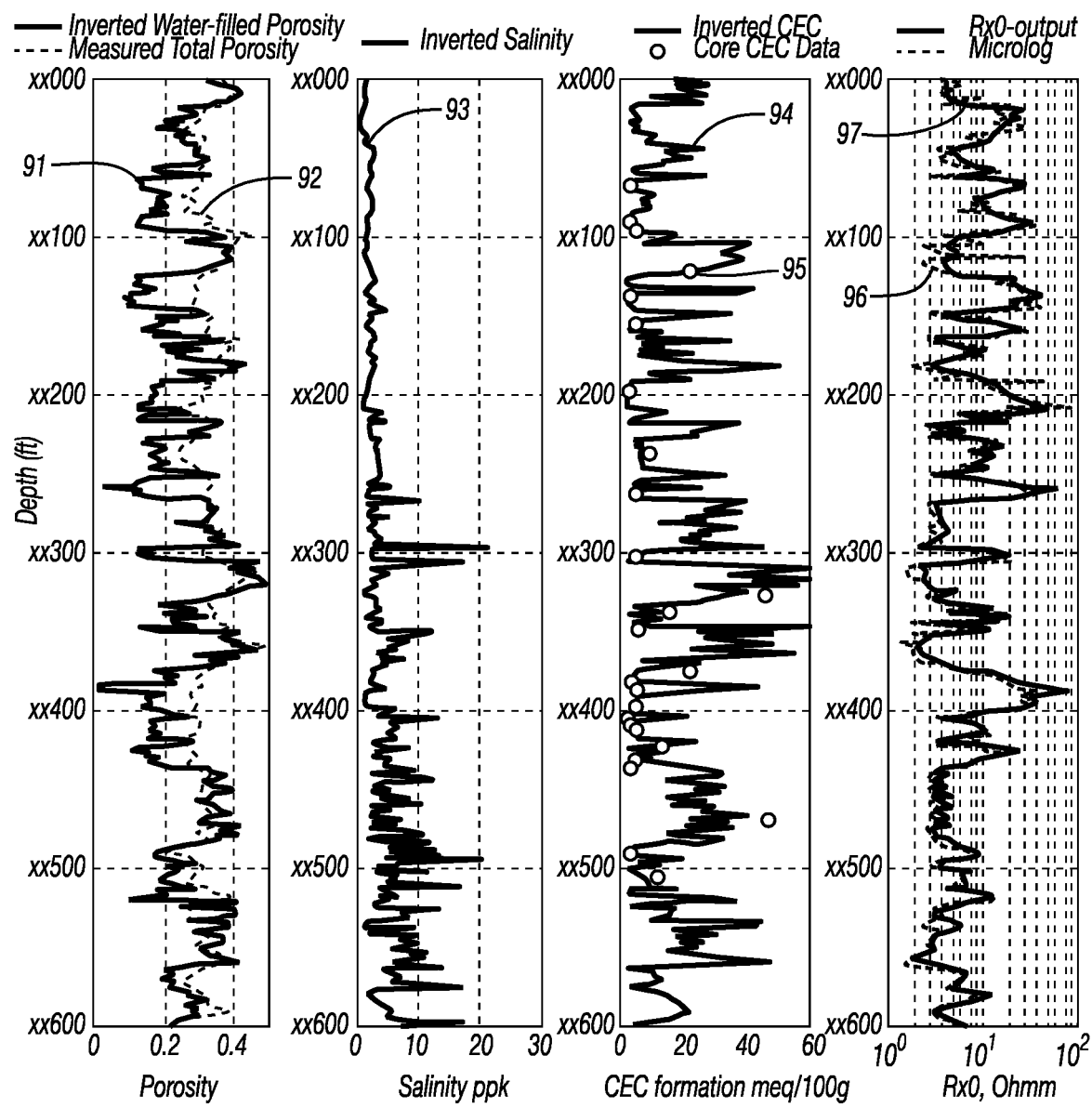
FIG. 9 are plots of fitted water-filled porosity compared with total porosity, fitted salinity, fitted CEC and measured CEC, and fitted Rxo and measured Rxo in accordance with one or more example embodiments.

FIG. 8 are plots of a model-fitted permittivity 82 and a model-fitted conductivity 84 compared to measured data from a log of a shaly sand. FIG. 9 are plots of fitted water-filled porosity 91 compared with total porosity 92, fitted salinity 93, fitted CEC 94 and measured CEC 95, and fitted Rxo 96 and measured Rxo 97.

The schematic representation in FIG. 10 is another embodiment of a general mixing scheme for a physics-based dielectric dispersion model of clay-containing rocks. The model is applicable not only to shaly sand formations, but any other formation containing clays such as non-conventional reservoirs (gas shales, oil shales, shale oil and clay-containing carbonates). The formation is represented by the following major constituent fractions: mineral matrix, clay particles coated with bound water and surrounded by the electrochemical double layer and free water. The mineral matrix phase includes all minerals in case more than one mineral is present. The permittivity and conductivity of the combined mineral phase is estimated using either a physics-based geometric dispersion models such as the textural or bimodal model (or any other geometric model) or an empirical mixing rule, such as, CRI.

In some embodiments, the second model involves a first step of calculating the dielectric response of the non-clay mineral phase and free water, and a second step of mixing of the clay particles coated by the bound water and surrounded by the electrochemical double layer into the background phase. To compute the formation dielectric response, the background dielectric response of the non-clay mineral phase and free water is first calculated, and the dielectric response of the background phase is estimated based on the CRI model or geometric dispersion models such as the textural or bimodal model (or any other geometric model). The mineral inclusions may have a shape of spheroid thus allowing textural variability of the rock to be taken into account via geometric model. The porosity of the background phase, $\phi_1 = \phi/(1-V_{clay})$, is higher than the total rock porosity, which reduces when the clay fraction is inserted into the background phase. A suitable physics based model may be used.

Examples of the mixing models that can be applied for estimating the properties of the background phase include the textural model (equations (8) and (9)), as well as the models given by the equations provided further below.

$$\epsilon_{cri} = \left((1-\phi)\sqrt{\epsilon_m} + \phi S_w \sqrt{\epsilon_w} + (1-S_w)\phi\sqrt{\epsilon_o}\right)^2 \quad (8)$$

$$\epsilon_{eff} = \epsilon_{cri} + \frac{\frac{1}{3}\sum_{j=1}^{n} f_i(\epsilon_j - \epsilon_{cri}) \sum_{i=1}^{3} \frac{\epsilon_{cri}}{\epsilon_{cri} + N_j^i(\epsilon_j - \epsilon_{cri})}}{1 - \frac{1}{3}\sum_{j=1}^{n} f_i(\epsilon_j - \epsilon_{cri}) \sum_{i=1}^{3} \frac{N_j^i}{\epsilon_{cri} + N_j^i(\epsilon_j - \epsilon_{cri})}} \quad (9)$$

The Complex Refractive Index Model:

$$\epsilon_h = \epsilon_{cri} = (\phi\sqrt{\epsilon_w} + (1-\phi)\sqrt{\epsilon_m}) \quad (10)$$

The Self-Similar Model:

$$\left(\frac{\epsilon_h - \epsilon_m}{\epsilon_w - \epsilon_m}\right)\left(\frac{\epsilon_w}{\epsilon_h}\right)^{1/3} = \phi \quad (11)$$

The Bruggeman Symmetric Model or Polder-Van Santent Model:

$$\phi\left(\frac{\epsilon_w - \epsilon_h}{\epsilon_w + 2\epsilon_h}\right) + (1-\phi)\left(\frac{\epsilon_m - \epsilon_h}{\epsilon_m + 2\epsilon_h}\right) = 0 \quad (12)$$

where $\epsilon_w$ is the complex permittivity of water, $\epsilon_m$ is the permittivity of rock matrix and $\phi$ is the total formation porosity, and $\epsilon_h$ is the permittivity of background (host) medium. All of the above formula can be extended to the multi-component cases when the hydrocarbons are present or multiple minerals compose rock matrix.

In some embodiments, a next step in calculating the formation dielectric response includes mixing of the clay particles coated by the bound water and surrounded by the electrochemical double layer into the background phase. The clay particles generally have a shape of spheroid coated by the layer of bound water and EDL. A physics-based first principles model, described below, is used to compute the polarizability P of the clay particle coated by the layer of bound water and EDL in the presence of the applied electric field. Next the effect of this polarization on the rock's permittivity and conductivity is evaluated using a physics based mixing law. For example, the mixing carried out using the Maxwell-Garnett approach as shown below:

$$\epsilon_{eff} = \epsilon_h\left[\frac{1 + 2 \cdot V_{cl} \cdot P}{1 - V_{cl} \cdot P}\right] \quad (13)$$

where $\epsilon_{eff}$ is the effective permittivity of the shaly-sand formation, $\epsilon_h$ is the effective permittivity of the background (host) medium, P is the polarizability of a clay particle and $V_{cl}$ is the volumetric fraction of clay. Instead of the Maxwell-Garnett rule other type of mixing models can also be applied. However, the equations for the EDL polarization are all stated in terms of particle polarizability and the mixing model has to be formulated also in terms of the polarizability of the inclusions with EDL, similarly to the equation (13).

Modeling of the Clay Particle

In accordance with the present techniques, a clay particle modeling technique may be used. Clay particles have negative charges embedded in them, usually due to substitutions in the clay lattice. Outside the clay particles, there are positive charges (cations) that compensate the negative charges inside the clay grain. Some of these positive charges are bound to the surface and are not that mobile. This layer of charges is called the Stern layer. At high frequencies, an assumption may be made that they cannot move fast enough to respond to the electric field and that their main effect is to reduce the apparent charge of the clay particle. Alternate models of the Stern layer will be given below.

The remainder of the compensating charges are free to move within the double layer, and they cause the dielectric response at high frequencies. The integral of the density of these charges, from the surface of the clay particle to the outer edge of the double layer, may be referred to as the surface charge density, or surface charge. Typically, in dielectric models of clay, it is assumed that the surface charge is uniformly distributed around the spheroid. However, depending on how the negative charges embedded in the clay are distributed, the distribution of the surface charge will be different. While a uniform charge distribution case will be discussed in detail in this disclosure, in accordance with the present techniques, other non-uniform cases are also applicable. Techniques involve solving for the dielectric response of a charged spheroid at high frequencies. Under such circumstances, it may behave as if it is a conducting particle, with different conductivities depending on whether the electric field is perpendicular or parallel to the axis of symmetry.

To represent this solution, a spheroid may be used. The parameter a represents half the major axis of the spheroid, and b represents half the minor axis of the spheroid, and the aspect ratio is b/a. A spheroidal coordinate $\xi_0$ is defined in Equation (6) above. When the grains are platy and the aspect ratio is small (e.g., b/a≤0.1), then the spherical coordinate $\xi_0$ may be approximately equal to b/a. The volume of a spheroid is given by $$V = \frac{4}{3}\pi a^2 b. \quad (14)$$

The surface area of an oblate spheroid is given by $$S = 2\pi a^2 \left(1 + \frac{1-e^2}{e} \tanh^{-1} e\right), \quad (15)$$

The eccentricity of the spheroid is represented by $e=1-b^2/a^2$. When the surface charge is uniform, the surface charge density may be represented as $e_0 \Gamma_+$ where $\Gamma_+$ is a constant and $e_0$ is the charge of an ion.

The dielectric properties of clay particles surrounded by the electrochemical double layer are computed following theories developed for EDL polarization response. The present techniques and work flow may apply to current and future models. For example, models such as the Chew-Sen approach, the Chassagne-Bedaux approach and the first principles approach leading to Equations (18) through (26) below are appropriate for addressing diffuse layer polarization.

In the Chew-Sen approach, dielectric enhancement caused by the double layer polarization is calculated using the "thin double layer approximation," assuming that thickness of the double layer is much less than the size of the particle. The effective dipole moment of a single particle suspended in an electrolyte is defined according to equation:

$$P \sim -\frac{1}{2} + \left(\frac{\delta}{a}\right)\frac{6t^2}{1-t^2} + \\ \left(\frac{\delta}{a}\right)^2\left[-\frac{3}{4}\frac{i\omega}{D}\frac{\epsilon_p}{\epsilon'}a^2 + 6\ln(1-t^2) - \frac{24t^2}{(1-t^2)^2}\left(t^2 + \frac{1}{\alpha}\right)\right] \quad (16)$$

An example of a large dielectric enhancement predicted with thin double layer model for polystyrene particles suspended in electrolyte solution is shown in FIG. 11, which plots the prediction of the thin double layer model of the values of the real and imaginary parts of the dielectric constant of polystyrene particle suspended in electrolyte solution. Large dielectric enhancement is predicted due to double layer polarization. In the Chassagne-Bedaux approach, dipolar coefficients of a spheroidal particle surrounded by the EDL are represented by the following formula:

$$P_i = \frac{\begin{pmatrix}\tilde{K}_2 - \tilde{K}_1 + 3(1-L_i)[\tilde{K}_{par}^- + \tilde{K}_U^- + \kappa_{par}^{extra}] + \\ 3L_i[\tilde{K}_{per}^- + \kappa_{per}^{extra}]\end{pmatrix}}{3\tilde{K}_1 + 3L_i(\tilde{K}_2 - \tilde{K}_1) + 9L_i(1-L_i)} \\ [\tilde{K}_{par}^-(a/r_0)^3 + \tilde{K}_U^-(a/r_1)^3 + \kappa_{par}^{extra} - \tilde{K}_{per}^- - \kappa_{per}^{extra}] \quad (17)$$

where i=n, p indicate the directions normal and along the axis of symmetry of the spheroid, respectively. $\tilde{K}_2$ is the complex conductivity of the core material of the EDL particle and $\tilde{K}_1$ is the complex conductivity of the bulk electrolyte.

Past techniques for solving for polarization coefficient of a charged spheroid have involved solving for the polarization coefficient at zero frequency. In accordance with the present techniques, polarization coefficient of a charged spheroid may be solved for high frequencies. In particular, the modeling may be suitable when $\omega \gg D/a^2$ where D is the diffusion coefficient of the cations and a is the size of the clay grain. This range of frequencies should include the frequencies measured by the dielectric dispersion logging tools. A first-principles calculation of the dielectric response of the clay particle can be obtained by solving the Poisson's equation and imposing charge conservation via a diffusion equation. According to this first-principles calculation of the dielectric enhancement due to the double layer, at these frequencies, the polarization coefficients $P_p$ along the axis of symmetry of the spheroid and $P_n$ perpendicular to the axis of symmetry have the form $$P_{p,n} = \frac{1}{3}\frac{\varepsilon_{p,n}^* - \varepsilon_w^*}{L_{p,n}\varepsilon_{p,n}^* - (1-L_{p,n})\varepsilon_w^*}, \quad (18)$$

where $L_p$ and $L_n$ are the depolarization factors along the axis of symmetry and perpendicular to the axis of symmetry, respectively. In the above equation, $\varepsilon_w^*$ is the complex permittivity of the bulk electrolyte and $\varepsilon_p^*$ and $\varepsilon_n^*$ are the effective complex permittivities of the clay particle parallel and perpendicular to the axis of symmetry, respectively. They are given by $$\varepsilon_{p,n}^* = \varepsilon_c + i\frac{\sigma_{p,n}}{\omega\varepsilon_0}, \quad (19)$$

where $\varepsilon_c$ is the actual permittivity of the clay particle and $\sigma_p$ and $\sigma_n$ are the apparent conductivities of the clay particle parallel and perpendicular to the axis of symmetry, respectively. We have found that, when the surface charge $\Gamma_+$ is uniformly distributed around the spheroid, the apparent conductivities have the form $$\sigma_p = f_p(\xi_0)\sigma_{eff}, \quad (20)$$

$$\sigma_n = f_n(\xi_0)\sigma_{eff}, \quad (21)$$

In these equations $f_n(\xi_0)$ is a function only of the aspect ratio (or $\xi_0$), and $\sigma_{eff}$ is the conductivity of brine with charge density equal to $\Gamma_+/a$. It equals the apparent conductivities $\sigma_n$ and $\sigma_p$ when the particle is a sphere. This effective conductivity is given by $$\sigma_{eff} = \frac{\Gamma_+}{a}\frac{2e_0^2 D}{k_B T}, \quad (22)$$

where D is the diffusion coefficient of the charges in the brine, $k_B$ is Boltzmann's constant, T is the temperature in Kelvin, and $e_0$ is the electric charge of the cations in the brine.

When the aspect ratio is much less than one, the geometrical factors, $f_p(\xi_0)$ and $f_n(\xi_0)$, are given by $$f_p \approx -\frac{3}{2}\xi_0 \log \xi_0, \quad (23)$$

$$f_n \approx \frac{3}{4}\frac{1}{\xi_0}. \quad (24)$$

These solutions for the apparent conductivity are only first order solutions to the matrix equations for the dielectric response. When the second order solutions are included, the clay particles are no longer simply conducting particles with different conductivities along the two axes. However, the main effect of including the higher order corrections is to decrease $f_p$.

In another embodiment, the surface charge is non-uniform. If the surface charge is greater on the flat surface than on the rim, then $f_n$ is not affected much, but $f_p$ decays to zero much more quickly as the aspect ratio decreases than in the uniform surface charge case. For a particular non-uniform distribution of surface charge, we can solve exactly for the polarization coefficient. In that case, if the CEC is the same as in the uniform case, then, for small aspect ratios, $$\sigma_p = \frac{3}{2}\xi_0 \sigma_{\it{eff}} \qquad (25)$$

$$\sigma_n = \frac{3}{4}\frac{1}{\xi_0}\sigma_{\it{eff}}. \qquad (26)$$

The expression for $\sigma_n$ is identical to the one for $\sigma_n$ for uniform surface charge density at small $\xi_0$. The polarization coefficient in the Chassagne-Bedaux approach of equation (17) above also reduces to the form in equation (18) at high frequency, but with different values for $\sigma_n$ and $\sigma_p$ In yet another embodiment of the invention, we can take $\sigma_p=0$, while still using equation (21) for $\sigma_n$. These versions of the polarization coefficients, or other suitable expression for the polarization coefficient, may all be used for the clay grains with an electrical double layer at high frequencies.

Relationship Between Zeta Potential and the CEC:

When clays are involved, the CEC is more commonly used than surface charge density. The CEC is the amount of charge (in milliequivalents) per hundred grams of clay. If $\rho$ is the density of the clay, then the CEC is given by $$\frac{CEC}{100} = \frac{1}{\rho}\frac{1}{V} e_0 \Gamma_+ S. \qquad (27)$$

When some of the charges are in the Stern layer, the surface charge density, $\Gamma_+$ will be reduced. In particular, if $f_{stern}$ is the fraction of the charges in the Stern layer, then equation (27) becomes $$\frac{CEC}{100}(1 - f_{stern}) = \frac{1}{\rho}\frac{1}{V} e_0 \Gamma_+ S. \qquad (28)$$

Then, when the surface charge density is uniform and the aspect ratio is small, the CEC can be related to $\Gamma_+$ as follows:

$$CEC = \frac{100}{\rho}\frac{3}{2}\frac{e_0 \Gamma_+}{b}\frac{1}{(1 - f_{stern})}. \qquad (29)$$

where units=9.64×10$^7$ is a conversion factor to obtain milliequivalents when density is in g/cm$^3$ and the charge is in Coulombs.

Similarly, when $\xi_0 \ll 1$, the conductivity when the electric field is perpendicular to the axis of symmetry (and along the flat face of the spheroid) becomes $$\sigma_n = \frac{3}{2}\frac{1}{\xi_0}\frac{\Gamma_+}{a}\frac{e^2 D}{k_B T}. \qquad (30)$$

Eliminating $\Gamma_+$ from these two equations, we find $$CEC = \frac{100}{\rho}\frac{k_B T}{eD}\frac{1}{(1 - f_{stern})}\sigma_n. \qquad (31)$$

When the aspect ratio is small, the CEC of the clay may be directly proportional to $\sigma_n$. The constant of proportionality depends on the density of the clay, temperature and the diffusion coefficient of the ions. The density of clay does not vary much. The temperature can vary more, but it is measured in degrees Kelvin, which reduces the effect. The diffusion coefficient will also increase as the temperature is increased. In addition, $f_{stern}$ can depend on clay type, and also, possibly, on pH.

The CEC in equation (31) is the CEC of the individual clay grains. To obtain the CEC of the whole rock, this value may be multiplied by the weight fraction of the rock matrix that is clay.

Physical models of the EDL layer polarization commonly use the value of the particle's zeta potential in their formulation. The zeta potential values are linked to the useful petrophysical quantities of CEC (or Qv). For a spherical particle the zeta potential is related to the particle charge via the following equation:

$$Q = -16\pi a^2 N_0 e\delta\left[\sinh\frac{\Psi_0}{2} + \frac{2\delta\tanh\Psi_0/4}{a}\right] \qquad (32)$$

where $\Psi_0$ is the zeta-potential, a is the particle radius, $\delta$ is the Debye screening distance and $N_0$ is the charge density far away from the particle.

Assuming a pack of spherical grains the cation exchange capacity (CEC) and charge per unit pore volume, $Q_v$, can be related to the particle surface ion density, $\Omega_+$:

$$Q_v = \frac{3\Omega_+}{a}\frac{1 - \phi}{\phi} = (CEC/100)\rho_g\frac{1 - \phi}{\phi} \qquad (33)$$

where, $\phi$ is the rock porosity and $\rho_g$ is the grain density. A similar equation can be obtained for spheroidal clay particles. The equations (32) and (33) can be recast to determine zeta-potential from the CEC or Qv value as shown below:

$$t = \tanh\frac{\Psi_0}{4}$$

$$A = -e \cdot 24\frac{(1 - \phi)}{\phi}N_0\frac{\delta}{a}$$

$$B = \frac{\delta}{a}$$

$$A \cdot B \cdot t^3 - Q_v \cdot t_2 - A \cdot (B + 1) \cdot t + Q_v = 0$$

Figure 12:
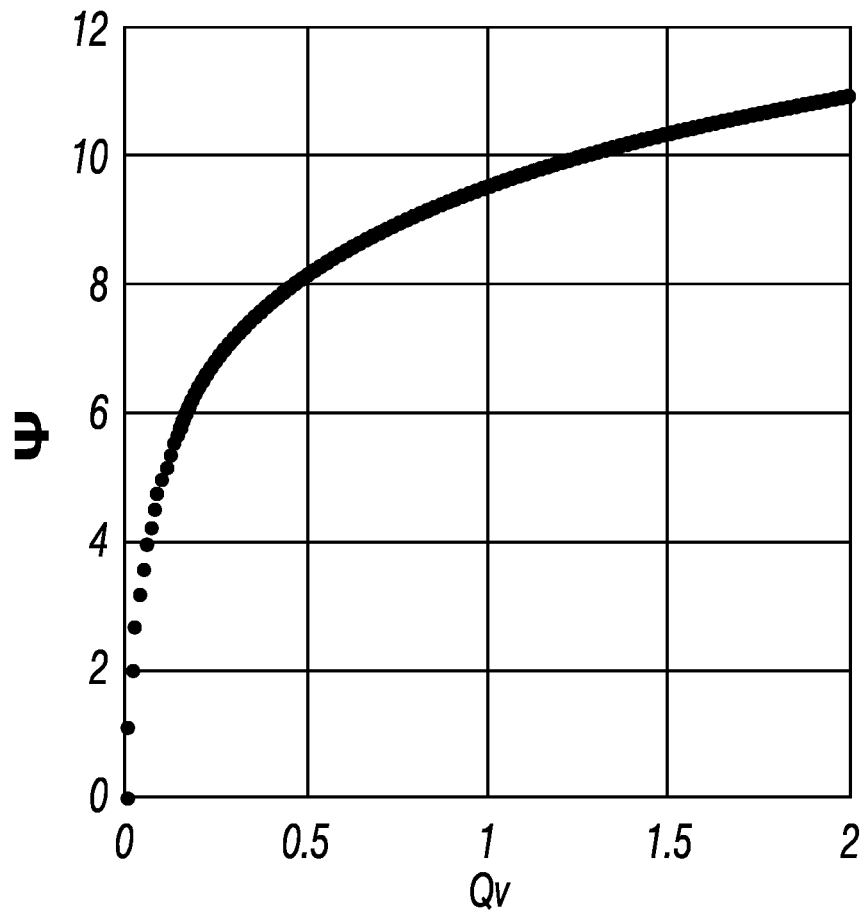
FIG. 12 is a plot of the dependence of the zeta potential value on Qv in accordance with one or more example embodiments.

The dependence of the zeta potential $\Psi$ on Qv for is shown in FIG. 12 for the following set of parameters: $N_0=2.08 \cdot 10^{25}$, T=298.14 K, a=0.094·10$^{-6}$, $\phi$=0.3. FIG. 12 plots the dependence of the zeta potential value on Qv. Shaly sands commonly contain at least two mineralogical fractions: clay and non-clay minerals such as quartz. The clay fraction is the dominant source of the overall rock's Qv (mixture of clay and quartz) is calculated as follows:

$$Q_v = \frac{V_{clay} \cdot \rho_{clay} \cdot (CEC_{clay}/100)}{\phi} \quad (34)$$

where $V_{clay}$ is the volumetric fraction of clay in [V/V], $\sigma_{clay}$ is the density of clay in [gr/cm³], $\phi$ is the total rock porosity in [V/V], and $CEC_{clay}$ is the clay cation exchange capacity in [meq/100 gr].

Cementation Exponent and Rxo

In accordance with the present techniques, both the cementation exponent and the low frequency conductivity in the invaded zone, Rxo, can also be determined from the shaly sand model. For low frequencies, when $\sigma_w > \sigma_n$ and $\sigma_n \gg \sigma_p$, Equation 5 reduces to $$\sigma_r = \phi^w(\sigma_w + B(\phi,p,d_L)\sigma_n), \quad (35)$$

where the cementation exponent, w, is given by $$w = \frac{3}{2}(1-p) + \frac{p}{3d_L}\frac{2+3d_L}{2-d_L}, \quad (36)$$

and $B(\phi, p, d_L)$ is a function of $\phi$, p, $d_L$ and the permittivity of the rock matrix. If the model is used to invert for p and $d_L$, then the cementation exponent can also be determined from Equation (36).

The resistivity of the rock at low frequencies is given by Equation (35). If the model is used to invert for porosity, p, and $d_L$, then Equation (35) can be used to determine the low frequency conductivity of the formation, $\sigma_r(\omega=0)$. The low frequency resistivity in the invaded zone, Rxo, is then given by $$R_{xo} = 1/\sigma_r.$$

In some embodiments, Equation (3) is strictly valid only for high enough frequencies, where $\omega \gg D/a^2$, where D is the diffusion coefficient of the cations and a is the size of the clay grain. At lower frequencies, the charges outside the double layer can also contribute to the permittivity and conductivity in response to the clay. Two such examples are given in Equations (16) and (17). Another example, found by solving for the polarization due to a charged spheroid at zero frequency, is given by $$P_{p,n} = \frac{1}{3}\frac{\sigma_{p,n} - \sigma_w^{p,n}}{L_{p,n}\sigma_{p,n} + (1-L_{p,n})\sigma_w^{p,n}}, \quad (37)$$

where $\sigma_{p,n}$ are defined in Equations (20) and (21), $L_{p,n}$ are the depolarization factors, and $\sigma_w^{p,n}$ are the effective water conductivity along the axis of symmetry and perpendicular to the axis of symmetry due to the presence of charged clay grains, respectively.

An even further improved method for determining $\sigma_r(\omega=0)$ and Rxo is to use these low or zero frequency solution for the polarization of a spheroid, in place of Equation (18), to derive a formula using a differential effective medium approach for computing the rock conductivity $\sigma_r(\omega=0)$ at zero frequency. From equation (37), we found that the porosity of the rock is related to the conductivity of water and to the rock conductivity $\sigma_r(\omega=0)$ at zero frequency. The resultant formula reads $$\phi = \prod_{i=0}^{2}\left(\frac{\sigma_w - r_i^{\omega=0}}{\sigma_r(\omega=0) - r_i^{\omega=0}}\right)^{p_i^{\omega=0}}. \quad (38)$$

Here, $r_0^{\omega=0} = 0$, $r_{1,2}^{\omega=0}$ are roots of a quadratic polynomial, and $p_{0,1,2}^{\omega=0}$ are residues of a rational functions, akin to situation in equation (3).

Including Hydrocarbons

Hydrocarbons can be included by several methods, including conventional methods for rocks without clay. For example, the non-conducting phase of the rock matrix (the non-clay grains) can be combined with the hydrocarbons via the CRI model, and then the resulting permittivity and conductivity can be used in place of the rock grains in the shaly sand model. Alternatively, the hydrocarbon can be accounted for by additional spherical inclusions, which for example, are added with the rock grains and clay grains via the differential effective medium mixing law. Another method for including hydrocarbons is to include them as a mixture of spherical and spheroidal grains, as in the Feng-Sen model. If hydrocarbons are included in the model, then the total porosity can be used as an input, and the water saturation can be inverted for, in addition to the water-filled porosity.

Stern Layer Contribution

The dielectric response of Stern or "fixed" double layer assumes that charges in the fixed layer will migrate only in a direction that is tangential to the particle surface and omits any flux of charge into, or out of, the bulk solution. These charges in the fixed layer may be assumed to move so slowly that they do not affect the dielectric response at high frequencies. Alternatively, they can be modeled by a model such as the Schwarz model. The equations below represent the Schwarz model, which results in a frequency-dependent permittivity and conductivity response:

$$\epsilon_f = \frac{\epsilon_s}{1+\omega^2\tau^2} \quad (39)$$

$$\sigma_f = \frac{\epsilon_s\omega^2\tau}{1+\omega^2\tau^2} \quad (40)$$

$$\epsilon_s = \frac{eR\Sigma_f}{kT} \quad (41)$$

$$\tau = \frac{R^2}{2\mu kT} = \frac{R^2}{2D} \quad (42)$$

where $\epsilon_f$ represents the dielectric constant due to Stern layer, $\sigma_f$ represents the conductivity due to Stern layer, $\omega$ represents the angular velocity, e represents the electronic charge, R represents the particle radius, $\Sigma_f$ represents the surface charge carrier density in the fixed layer (number of charges per square meter), k represents the Boltzman's constant, T represents the absolute temperature, $\mu$ represents the surface ionic mobility of counterions in fixed layer, and D represents the diffusion coefficient of counterions in fixed layer.

The above equations for the dielectric constant and conductivity caused by the Stern layer ma be further recast in terms of the complex conductivity and included in the EDL polarization model via additional conductance $\overline{K_{per}^{extra}}$ and $\overline{K_{per}^{extra}}$ that corresponds to the contribution normal and along to the particle surface correspondingly.

Fluid Flow

The electrophoretic mobility is also included in the general equation for the EDL polarization via the term $\tilde{K}_U$. Equations for estimating the influence of the electrophoretic mobility may be found in Chassagne and Bedaux or any alternative formulation of the fluid flow effect (such as in Hinch, Fixman, or Chew) can be used.

Bound Water

Figure 13:
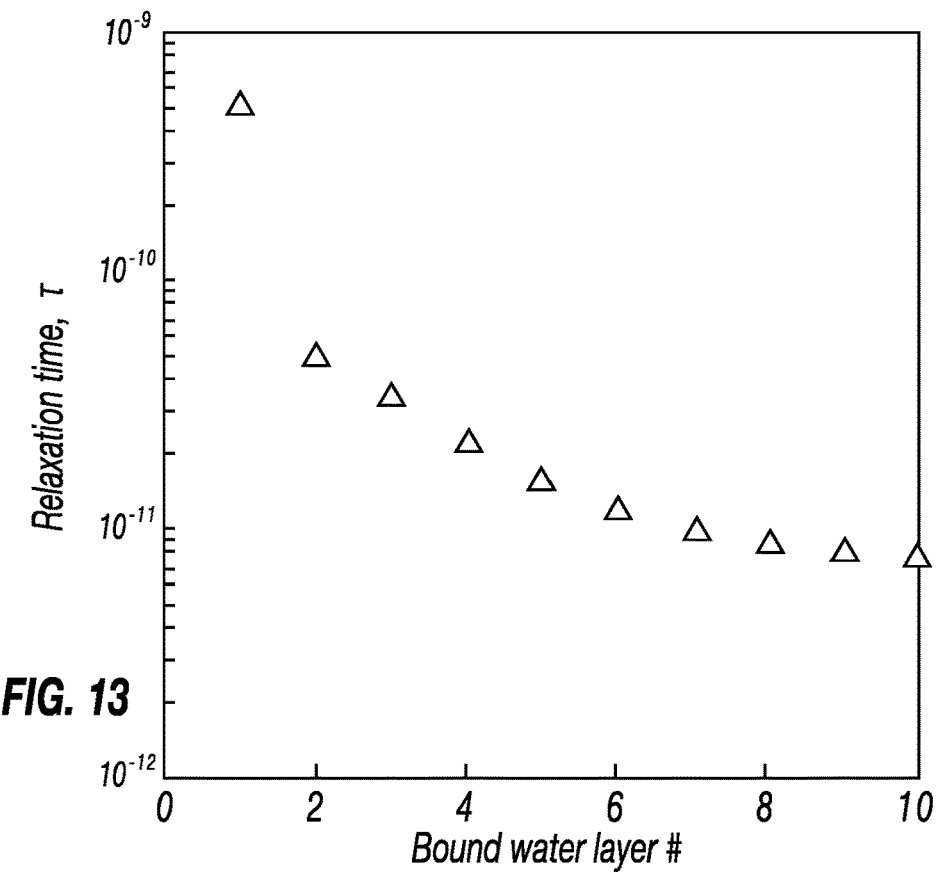
FIG. 13 is a plot of the dependence of the relaxation time of bound water in accordance with one or more example embodiments.
Figure 14:
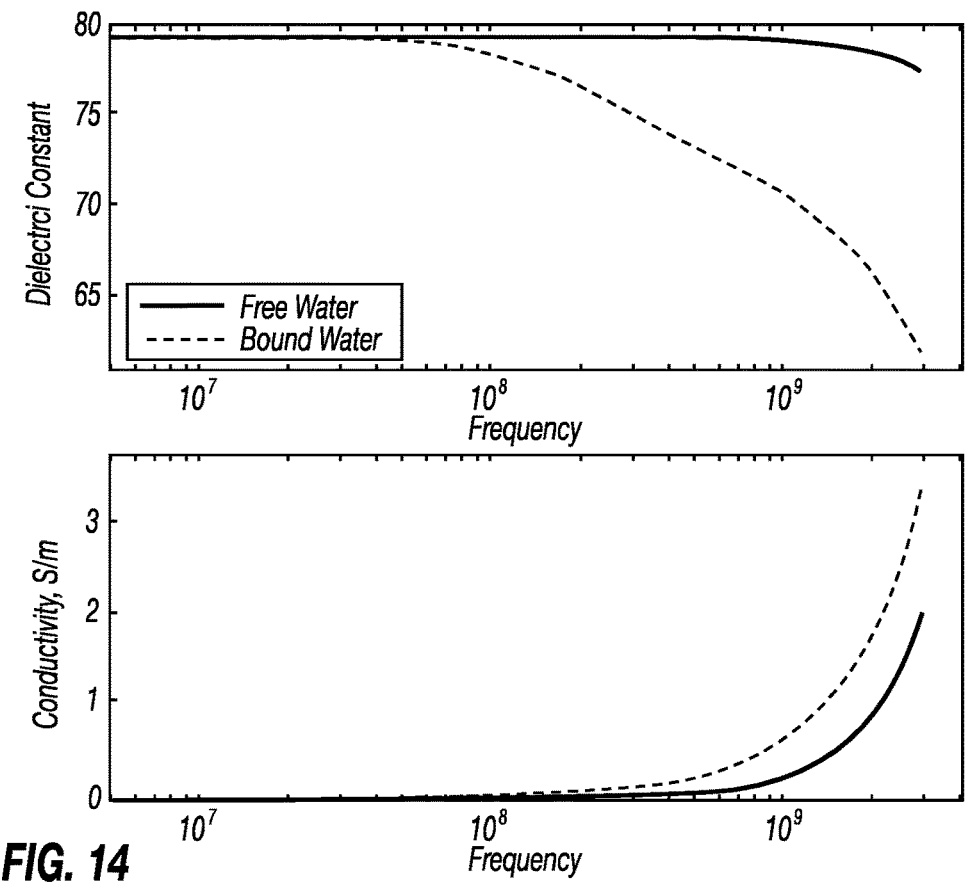
FIG. 14 is a comparison of the free and bound water dielectric conductivity dispersion curves in accordance with one or more example embodiments.

Clay-containing formations contain bound water that differs in its dielectric properties from free water. The bound water molecules are limited in their rotational freedom compared to free water molecules. Due to this effect the relaxation time of bound water differs from the relaxation time of free water as shown in FIG. 13, which plots the dependence of the relaxation time of bound water on the number of molecular layers away from the particle surface. The most tightly bound layers of bound water are situated against the particle surface and have the longest relaxation time. As the bound water molecules layers are situated farther away from the particle surface their relaxation time decreases finally reaching free water value at approximately 10 molecular layers. The difference in relaxation time leads to a decrease of the dielectric constant and an increase of the dielectric loss of the bound water compared to free water and frequencies above 100 MHz as shown in FIG. 14, which is a comparison of the free and bound water dielectric conductivity dispersion curves. The properties of the bound water are averaged over 10 monomolecular layers.

Figure 15:
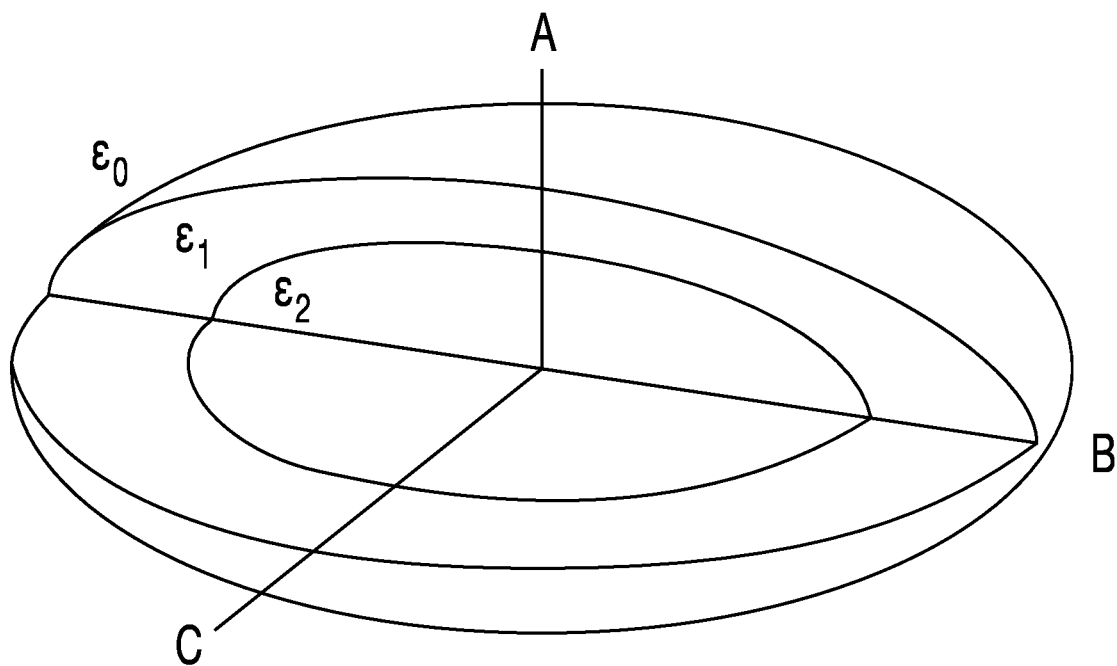
FIG. 15 is a schematic representation of a dry clay particle covered with a layer of bound water in accordance with one or more example embodiments.

The bound water properties can be include in the dielectric response of the clay particles by assuming layer of bound water coating the particle on the outside and calculating the effective dielectric constant of the spheroid consisting of the core dry clay particle and the external layer of bound water. The schematic representation of a dry clay particle covered with layer of bound water is shown in FIG. 15. Here, the dry clay particle with matrix permittivity $\varepsilon_2$ is covered with a layer of bound water with permittivity $\varepsilon_1$. The properties of bound water may be either averaged over several monomolecular layers or calculated as a layered ellipsoid with each layer representing monomolecular layers of bound water. The bound water properties are predicted based on the above mentioned theory (Schurr model) or any other description of the bound water response.

The specific surface area of main clays present in the oilfield formations is directly proportional to the formation CEC. The volume of bound water is calculated based on the specific surface area of clays contained in formation and using above mentioned relationship or any other correlation is linked to the formation CEC. Next the volume of bound water is subtracted from the total water volume, which yields effective porosity filled with free water. The bound water has been taken into account in the dual water model of conductivity of Clavier, Coates and Dumanoir.

Figure 16:
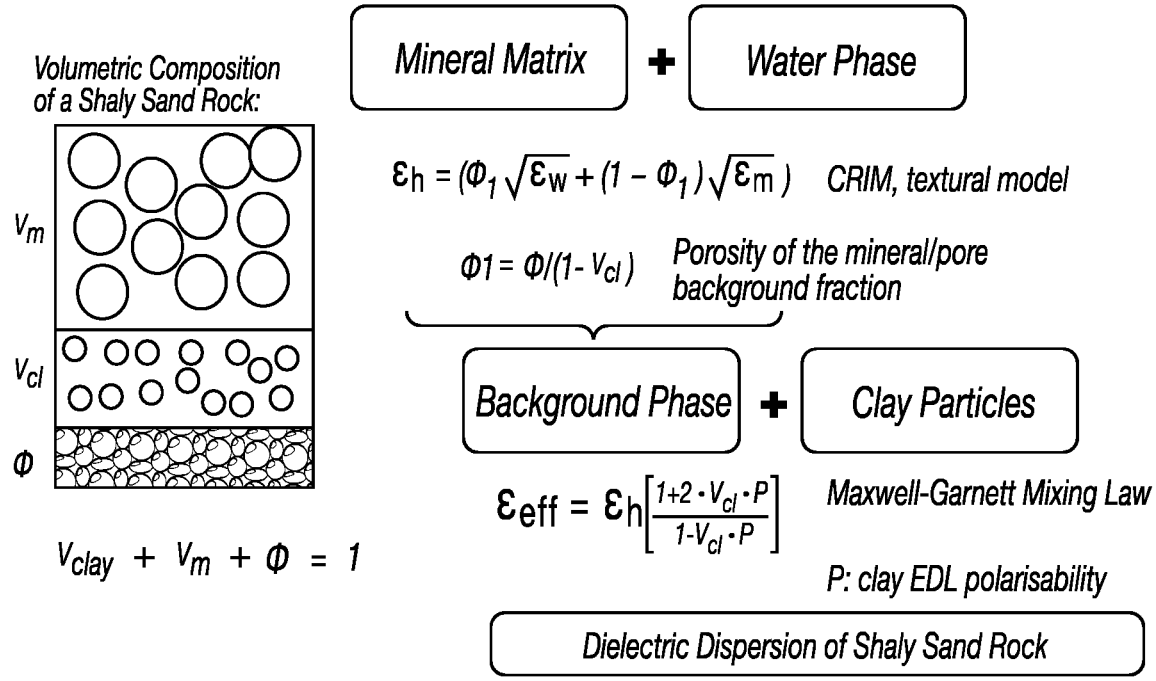
FIG. 16 is a schematic representation of a physics-based dielectric dispersion model in accordance with one or more example embodiments.

Examples of the New Physics-based Shaly Sand Model Predictions:

In one or more embodiments, a general approach on a specific implementation of the shaly sand model may be constructed out of listed possible variations of the model. A schematic representation of a physics-based dielectric dispersion model for clay-containing formations is shown in FIG. 16. In some embodiments, the background permittivity is computed based on the CRI mixing law and contributions of the Stern layer, bound water and fluid flow are omitted. In the general implementation of the model the particles are spheroids, but in this illustrative example, for simplicity, the particles are assumed to have spherical shape. The equation for clay particle polarizability takes the form:

$$P = \frac{\tilde{K}_2 - \tilde{K}_1 + 2\overline{K_{par}} + \tilde{K}_{per}}{\tilde{K}_2 + 2\tilde{K}_1 + 2\overline{K_{par}} - 2\tilde{K}_{per}} \quad (43)$$

$$\tilde{K}_2 = i\omega\epsilon_0\epsilon_{clay} \quad (44)$$

$$\tilde{K}_1 = \sigma_w + i\omega\epsilon_0\epsilon_{water} \quad (45)$$

where $\overline{K_{par}}$ and $\overline{K_{per}}$ are corresponding complex conductivities originating from the flux of ions along or perpendicular to the surface of the particle.

Figure 17:
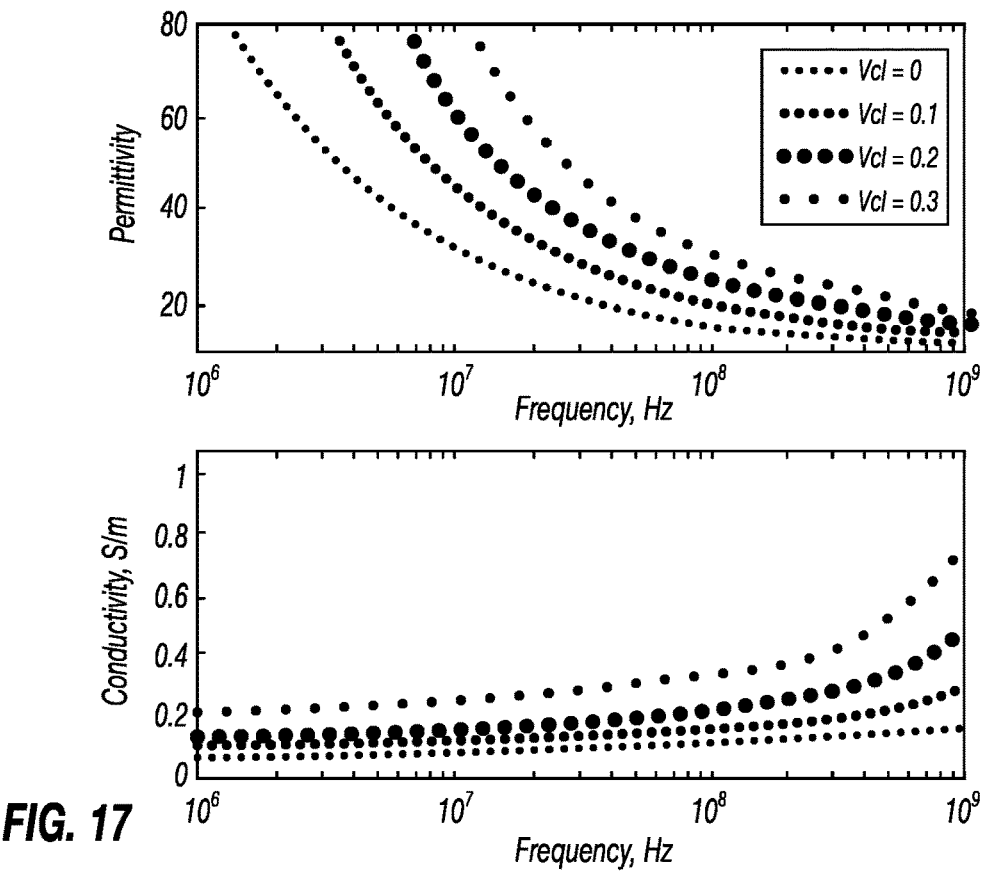
FIG. 17 is a response of the shaly sand model to variable CEC in accordance with one or more example embodiments.
Figure 18:
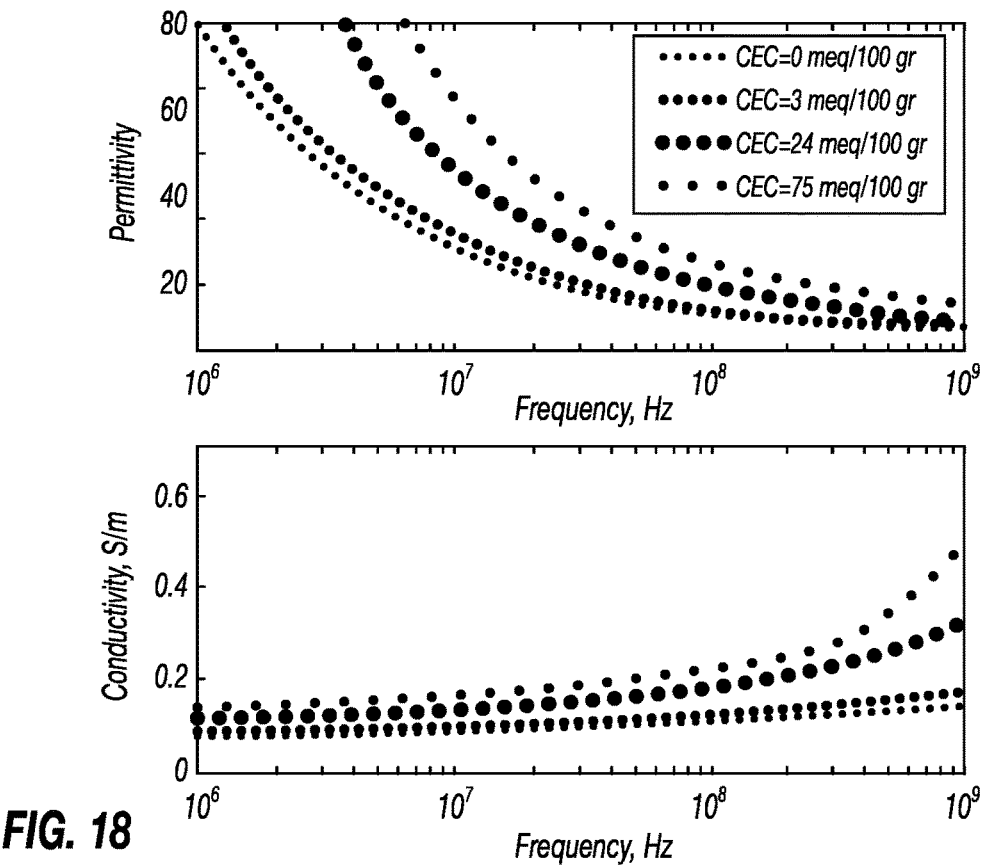
FIG. 18 is a response of the variable formation clay content to fixed CEC in accordance with one or more example embodiments.

The response of the new physics-based shaly sand model to variable CEC of the clay contained in the formation is shown in FIG. 17. The model predicts increased dielectric and conductivity dispersion with increasing clay CEC. The overall rock conductivity is also increasing with higher CEC values. The model response to variable formation clay content with fixed CEC value is shown in FIG. 18. The effect is similar to the previous case as increasing clay content with fixed CEC value has similar effect to increasing clay CEC while keeping the clay content constant.

Figure 19:
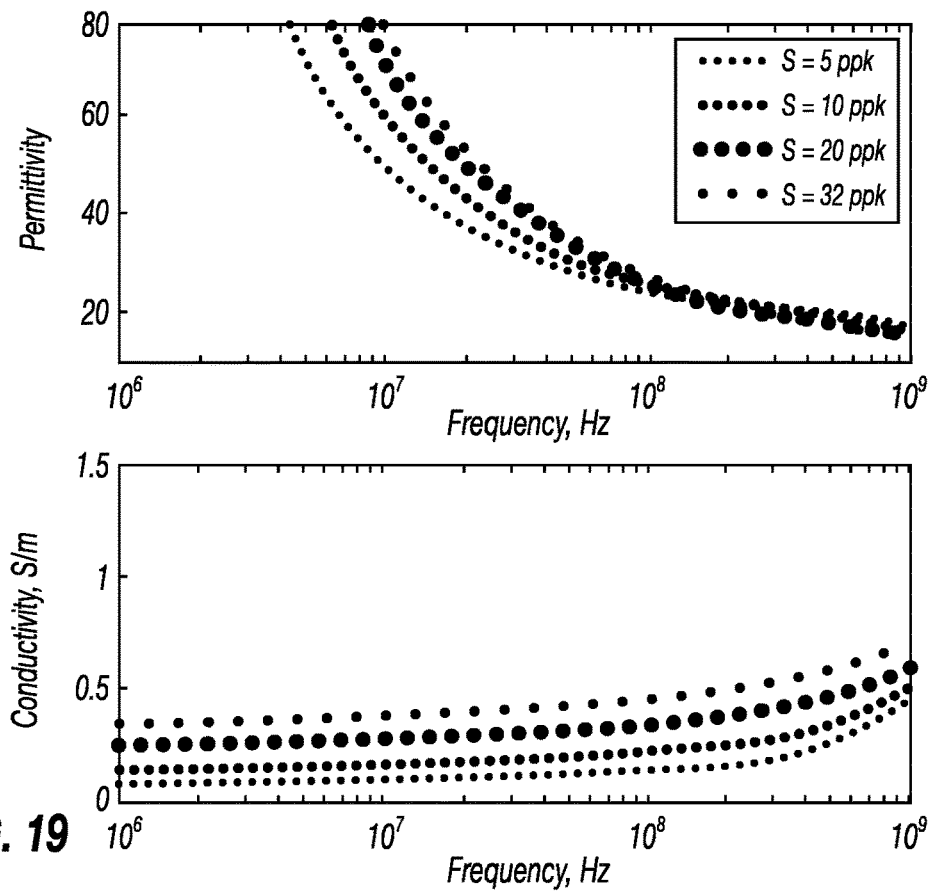
FIGS. 19 and 20 are plots of the effect of the formation water salinity in accordance with one or more example embodiments.
Figure 20:
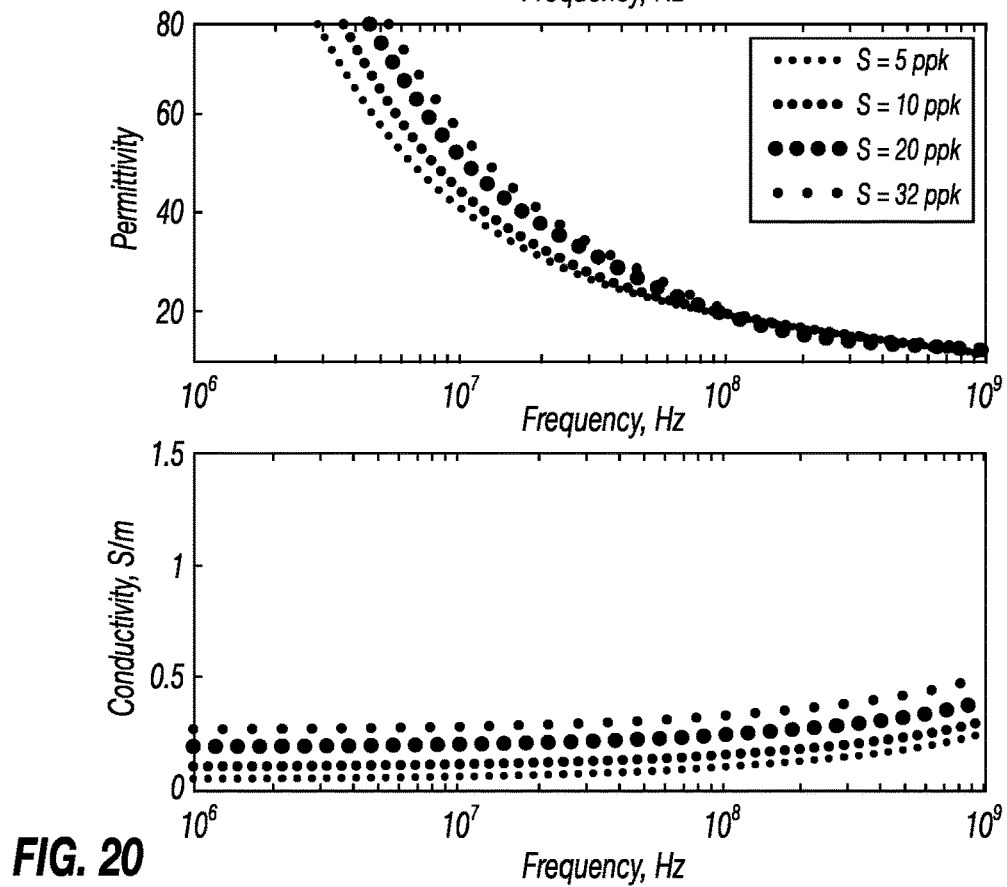

The effect of the formation water salinity is depictured in FIGS. 19 and 20. The model shows that the textural and EDL polarization effects both play a role in the overall rock response. For high CEC case (CEC=75 meq/100 gr) the decreasing brine conductivity diminishes the geometric polarization, but increasing EDL polarization compensates for this effect and the overall dielectric response in high frequency range does not change significantly. In the case of medium CEC clay (CEC=25 meq/100 gr) the decreasing textural polarization with decreasing brine salinity is not fully compensated by the increasing EDL polarization and there is a salinity dependence in the predicted dielectric dispersion curves.

In another embodiment of the model, the clay model given by Equations (18) through (26) is combined with the rock matrix, brine, and hydrocarbon with a differential effective medium model, such as the one described by Equations (3) through (7) and shown in FIG. 7. This model can be fit to dielectric dispersion data at multiple frequencies to obtain values for the water-filled porosity, the water salinity, the CEC, the aspect ratio or cementation exponent, and Rxo. An example of such a fit to log data of a shaly sand formation is shown in FIGS. 8 and 9. In FIG. 8, the fits to the permittivity and conductivity at the four tool frequency are shown. The log data is shown with solid lines and the fits are shown with dashed lines. In FIG. 9, the inverted values for the porosity, salinity, CEC and Rxo are shown. The shaly sand zones are characterized by high CEC and do not contain hydrocarbons. The hydrocarbon-bearing zones also have less clay and low CEC. The water-filled porosity found by the model is plotted with the solid line in Track 1, and the total porosity from the log data is plotted with a dashed line. In the shaly sand zones, the two porosities agree. In the hydrocarbon-bearing zones, the inverted water-filled porosity is lower than the total porosity by an amount consistent with the presence of hydrocarbons. In track 2, the inverted salinity is shown. The drilling mud is 3 ppk, and because the formation has high porosity, we expect the permeability to be high, and, hence the mud to invade the formation. The inverted salinity is consistent with the low value of salinity of the drilling mud. In Track 3, the inverted CEC is shown with the solid lines, and the CEC from core measurements is shown with the circles. Again, we get good agreement with the measurements. The last track shows the calculated Rxo compared with the measured value, which agree very well.

Enhanced Formation Evaluation by Combining the Formation Resistivity Measurements with the Dielectric Measurements:

As noted above, the formation resistivity depends on $Q_v$. In shaly sand models like Waxman-Smits or Clavier-Coats-Dumanoir correcting for $Q_v$ poses a great challenge. Thus using a dielectric derived $Q_v$ as an input, a better estimation of Sw can be made form the resistivity data.

Clay Typing:

In swelling clays, water can permeate in between the layers and can cause a great deal of expansion and even choke a formation. Furthermore the placement of the clay in the rock, such as pore lining or throat coating, can measurably affect rock properties, which may reflect in the dielectric response of the clay part that is inserted in the above workflow. Some embodiments modeling are therefore sensitive to clay typing and placement.

Typically, CEC per grain is related to the type of clay. For example, smectites often have a CEC of 70-100 me/100 g while illite typically has a CEC closer to 24 me/100 g. In some embodiments, the model gives the CEC per grain, which can be used in clay typing. If the CEC per grains falls within the range of smectites, the method would predict that the clay is predominately smectite, and similarly for illite and kaolinite. If it is between the typical values for the various clays, then the model predicts that it is a mixture of clay types.

Figure 21:
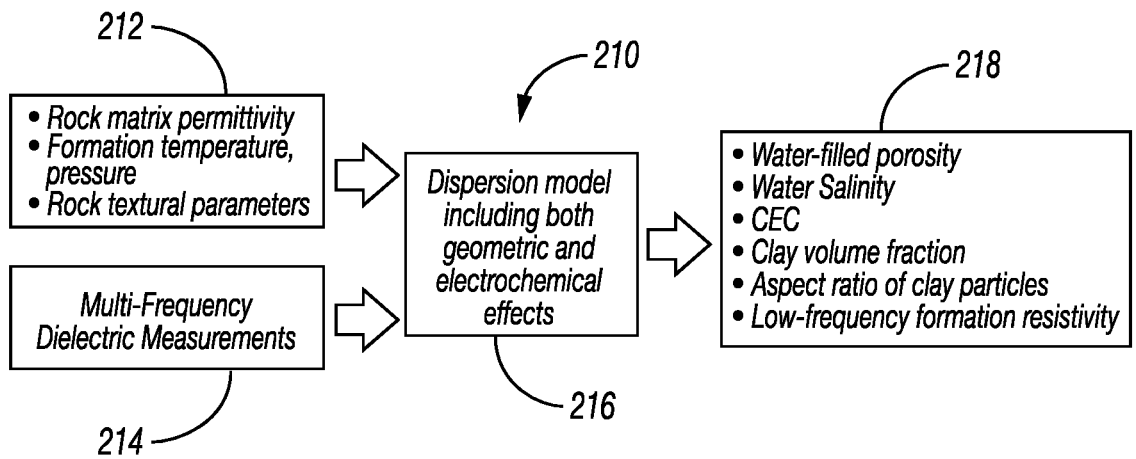
FIGS. 21-28 include workflows representing techniques for determining formation characteristics based on an inversion of formation data and measurements with multi-frequency dielectric data in accordance with one or more example embodiments.

Interpretation Schemes:

Based on the described novel method for combining textural and electrochemical effects, the present embodiments include several interpretation schemes for inversion of the multi-frequency dielectric data obtained with either downhole tool or in laboratory. For example, one embodiment as represented in workflow 210, depicted in FIG. 21, includes inputting data and parameters 212 related to the rock matrix permittivity, formation temperature, pressure, and multi-frequency dielectric measurements 214 into a dispersion model 216 including both geometric and electrochemical effects. The workflow 210 may be used for inverting the input data and measurements 212, 214 with the dielectric dispersion model 216 to determine outputs 218 including the water-filled porosity, water salinity, CEC, clay volume fraction, aspect ratio of the clay particles, and the low-frequency formation resistivity.

Figure 22:
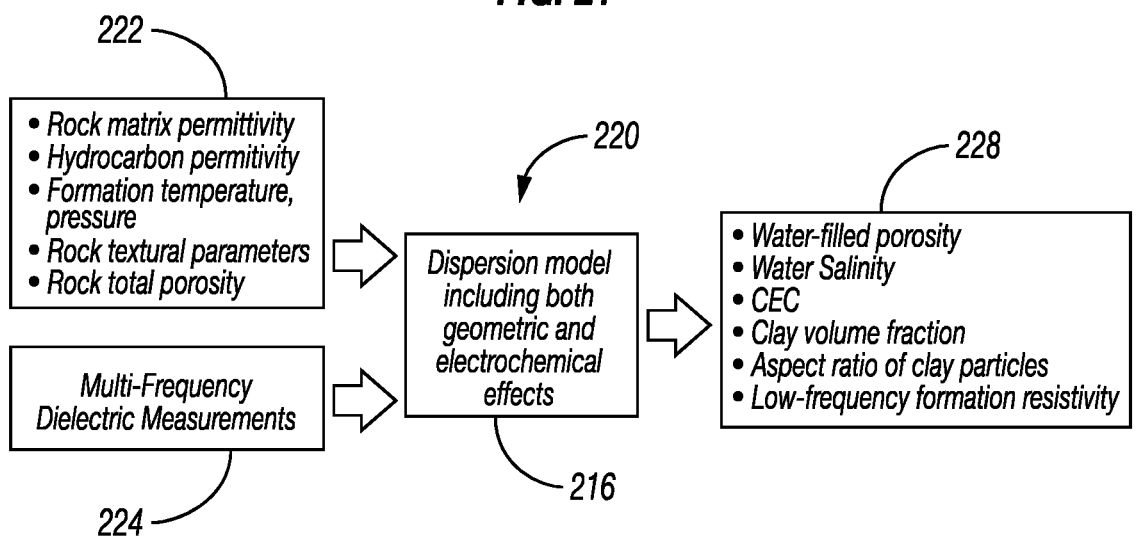

Another embodiment, as represented in workflow 220, as depicted in FIG. 22, the input data and parameters 222 include rock matrix permittivity, hydrocarbon permittivity, formation temperature/pressure, rock textural parameters, rock total porosity, and multi-frequency dielectric measurements 224. The input data and measurements 222, 224 is inverted with the dielectric dispersion model 226 to determine the outputs 228 including water saturation, water salinity, CEC, clay volume fraction, clay particle size, aspect ratio of the clay particles, and the effective textural parameters of the rock, low-frequency formation resistivity. This workflow 220 may be suitable in situations with relatively limited textural variability of clastic formations (e.g., where the formations are mostly clay), as it may be possible to fix textural parameters based on local knowledge or measurements in clean formations.

Figure 23:
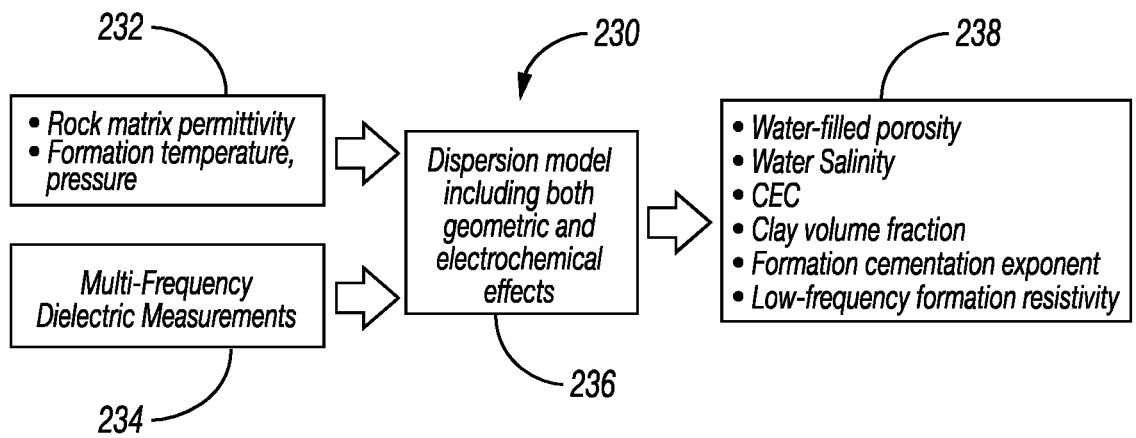

A workflow 230, as depicted in FIG. 23, involves data and parameter inputs 242 including rock matrix permittivity, formation temperature/pressure, and multi-frequency dielectric measurements 244. The input data and measurements 242, 244 may be inverted with the dielectric dispersion model 236 to determine outputs 238 including water-filled porosity, water salinity, CEC, clay volume fraction, formation cementation exponent and the low-frequency formation resistivity.

Figure 24:
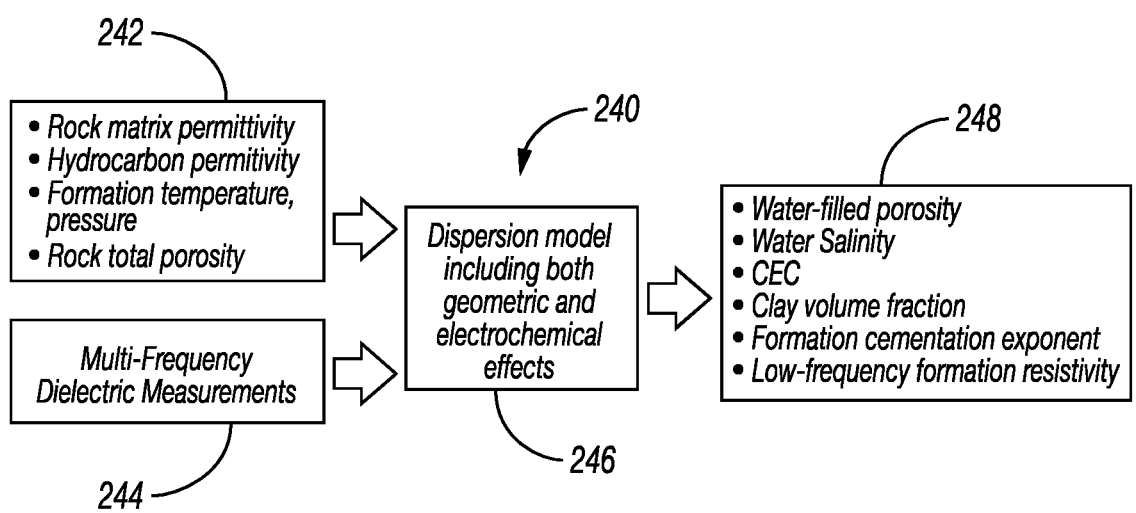

Another embodiment as depicted in the workflow 240 of FIG. 24 involves data and parameter inputs 242 including, rock matrix permittivity, hydrocarbon permittivity, formation temperature/pressure, rock total porosity, and multi-frequency dielectric measurements 244. The input data 242 and measurements 244, may be inverted with the dielectric dispersion model 246 to determine outputs 248 including formation water saturation, water salinity, CEC, clay volume fraction, formation cementation exponent and the low-frequency formation resistivity.

Figure 25:
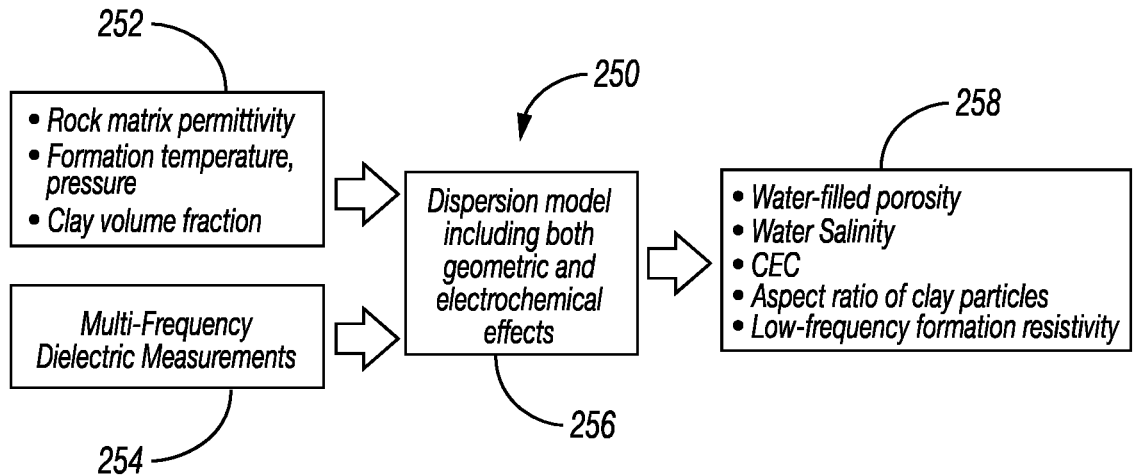

In another embodiment, a workflow 250 depicted in FIG. 25 may involve inputting data 252 including fixing the clay volume fraction and using the inversion of the data 252 and dielectric measurements 254 in the dispersion model 256 to output 258 formation water-filled porosity, water salinity, CEC, aspect ratio of clay particles and low-frequency formation resistivity.

Figure 26:
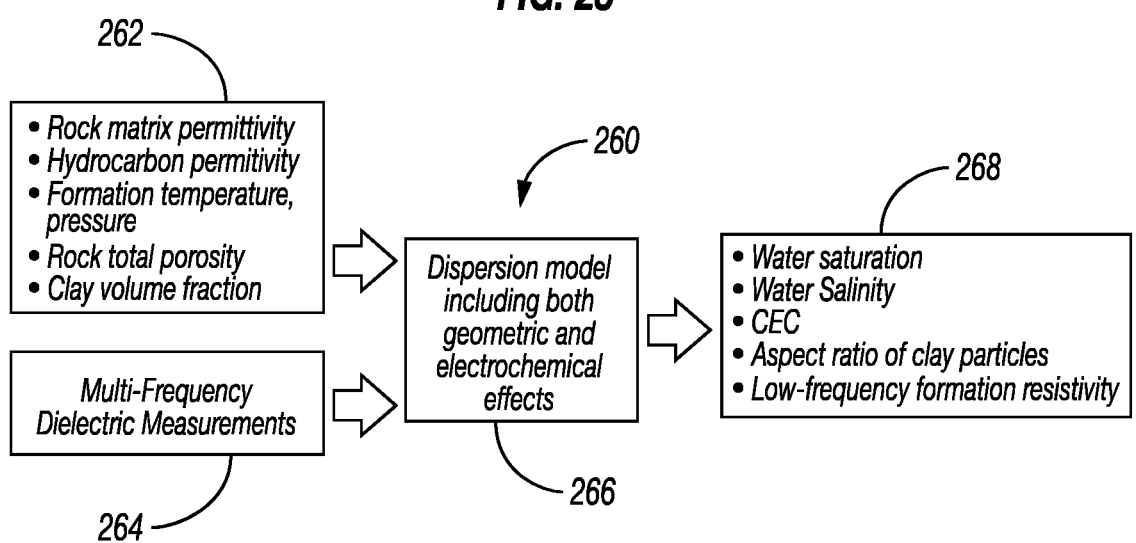

Another embodiment of a workflow 260 is shown in FIG. 26 where inputs 262 also include hydrocarbon permittivity and formation total porosity. In this case the inversion of the input data 262 and multi-frequency dielectric measurements 264 in the dispersion model 266 outputs 268 formation water saturation, water salinity, CEC, aspect ratio of clay particles and low-frequency formation resistivity.

Figure 27:
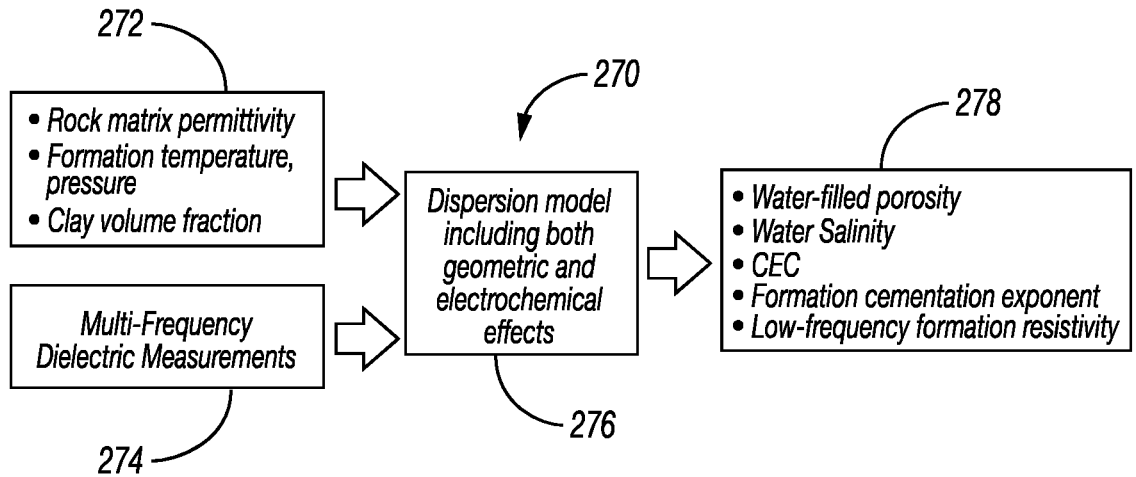

In some embodiments, workflow 270, as depicted in FIG. 27, involves input data and parameters 272 including rock matrix permittivity, formation temperature and pressure, clay volume fraction, and multi-frequency dielectric measurements 274. The input data and measurements 272, 274 may be inverted with the dielectric dispersion model 276 to determine outputs 278 including the water-filled porosity, water salinity, the CEC, formation cementation exponent, and the formation low-frequency resistivity.

Figure 28:
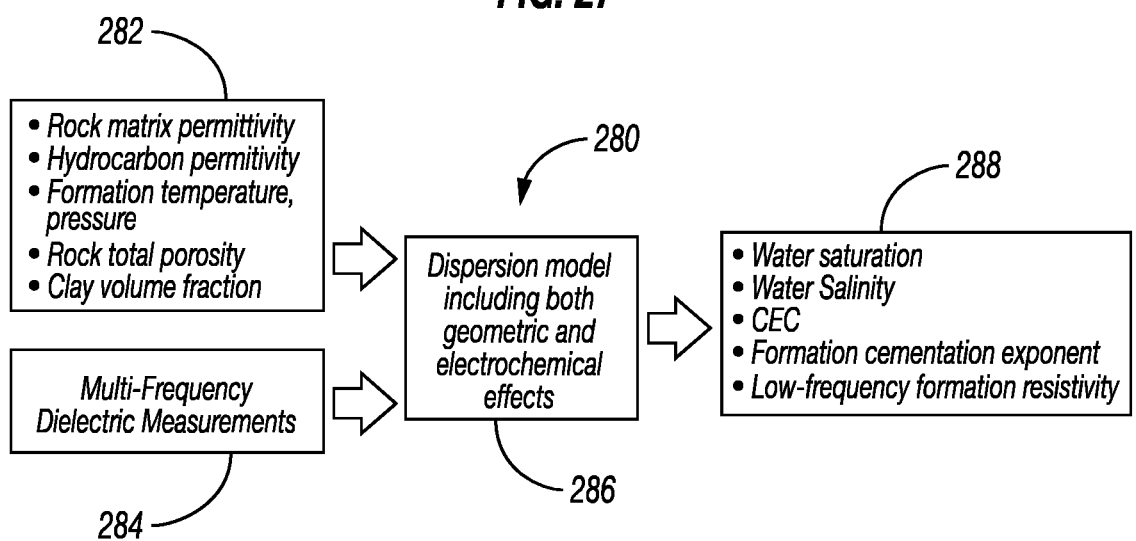

As depicted in FIG. 28, in some embodiments, a workflow 280 involves input data and parameters 282 including rock matrix permittivity, hydrocarbon permittivity, formation temperature and pressure, clay volume fraction, rock total porosity, and multi-frequency dielectric measurements 284. The input data 282 and measurements 284 may be inverted with the dielectric dispersion model 286 to determine outputs 288 including the formation water saturation, water salinity, the CEC, formation cementation exponent, and the formation low-frequency resistivity.

In some embodiments, if additional shapes are used in the mixing model, then the texture of the rock matrix may also be used an input for any of the workflows presented.

In accordance with the present techniques, embodiments are based on principles for combining geometrical and electrochemical effects that are responsible for the dielectric dispersion in fluid-saturated rocks and other porous media. One or more embodiments involve workflows based on this principle for determining the formation CEC, water-filled porosity and water salinity parameters using multi-frequency dielectric measurements. Embodiments also include incorporating geometrical effects of the rock grain shape on the dielectric response function of the clay-containing rock and combining geometric and electrochemical polarization effects to describe the overall response of clay-containing rock. Some embodiments involve combining multi-frequency measurements to obtain rock parameters to obtain petrophysical parameters of interest such as the CEC, water-filled porosity, water salinity, and water saturation. Techniques also involve obtaining bound water volume from an estimate of the formation CEC from the multi-frequency dielectric measurements independent of other measurements.

One or more embodiments involve the determination of the hydrocarbon content in shaly sands by incorporating CEC determined from the dielectric dispersion into the conductivity models.

The present techniques also involve conducting clay typing in combination with other measurements deriving total clay volume (gamma ray, nuclear spectroscopy, etc). Dielectric, CEC and other lab data can be incorporated into any of the workflows presented in this disclosure to further refine the model and improve its predictive power or any additional unknown rock properties.

In some embodiments, rock CEC values on cores may be determined from the multi-frequency dielectric measurements. Further, some embodiments include discrimination of swelling from non-swelling clays based on the formation CEC determined with the above methodologies.

While the embodiments are described with reference to various implementations and exploitations, it will be understood that these embodiments are illustrative and that the scope of the inventive subject matter is not limited to them. Many variations, modifications, additions and improvements are possible.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A method comprising:
    measuring multi-frequency dielectric measurements comprising dielectric measurements measured from a formation at a plurality of frequencies;
    inputting the multi-frequency dielectric measurements into a dispersion model, wherein the dispersion model comprises a relationship between a density of clay in the formation, a diffusion coefficient of one or more cations in brine, a fraction of the one or more cations in a Stern layer, and an apparent conductivity of one or more clay particles perpendicular to an axis of symmetry;
    determining a Cation Exchange Capacity (CEC) of a formation from inputting the multi-frequency dielectric measurements in the dispersion model;
    determining a characteristic related to a shape of the clay in the formation from inputting the multi-frequency dielectric measurements in the dispersion model; and
    applying the CEC and the characteristic related to a shape of the clay in the formation to resistivity logging data; and
    based on the resistivity logging data, determining an hydrocarbon content in the formation.

2. The method of claim 1, wherein the dispersion model accounts for geometrical and electrochemical effects of the multi-frequency dielectric properties of the clay in the formation and the formation over a frequency range.

3. The method of claim 2, wherein the dispersion model accounts for the geometrical and electrochemical effects based on combination of a first approach that determines an additional relationship between a porosity of rock, a conductivity of rock, and a conductivity of water or a second approach that determines an effective permittivity of a shaly-sand formation based on a polarizability of a clay particle, a volumetric fraction of the clay, and an effective permeability of a background medium with the dispersion model that assumes the formation comprises spherical, non-charged rock grains and spheroidal, charged clay grains with a fixed aspect ratio.

4. The method of claim 1, wherein the dispersion model is affected by a charge on the clay in the formation.

5. The method of claim 1, wherein the dispersion model comprises determining the CEC from the relationship below:

$$CEC = \frac{100}{\rho} \frac{k_B T}{eD} \frac{1}{(1-f_{stern})} \sigma_n,$$

where $\rho$ is the density of the clay in the formation, $k_B$ is Boltzmann's constant, T is a temperature of the formation in degrees Kelvin, D is the diffusion coefficient of cations in the brine in the formation, $f_{stern}$ is the fraction of the one or more cations in the Stern layer, e is a charge of the one or more cations, and $\sigma_n$ is the apparent conductivity of clay particles perpendicular to an axis of symmetry.

6. The method of claim 1, wherein the dispersion model comprises determining the CEC from the equations below:

$$t = \tanh\frac{\Psi_0}{4}$$

$$A = -e \cdot 24\frac{(1-\phi)}{\phi} N_0 \frac{\delta}{a}$$

$$B = \frac{\delta}{a}$$

$$A \cdot B \cdot t^3 - Q_v \cdot t^2 - A \cdot (B+1) \cdot t + Q_v = 0; \text{ and}$$

$$Q_v = (CEC/100)\rho\frac{1-\phi}{\phi},$$

where $\Psi_0$ is a zeta-potential of a particle of clay in the formation, $\alpha$ is radius of the particle of clay, $\delta$ is a Debye screening length, $N_0$ is a charge density far away from the particle of the clay, $Q_v$ is a charge per unit pore volume, $\phi$ is a porosity of rock in the formation, and $\rho$ is a density of the particle of clay.

7. The method of claim 1, comprising determining one or more other characteristics of the formation comprising a matrix permittivity of the formation, a temperature of the formation, a pressure of the formation, a rock texture of the formation, a total porosity of the formation, a clay volume fraction, and a clay grain size of the formation, or combinations thereof, to be input in the dispersion model.

8. The method of claim 7, comprising inverting the multi-frequency dielectric measurements and the one or more other characteristics of the formation with the dispersion model to further determine a water-filled porosity of the formation, a water salinity of the formation, or both.

9. The method of claim 7, comprising inverting the multi-frequency dielectric measurements and the one or more other characteristics of the formation with the dispersion model to further determine one or more the clay grain size, a water saturation, a cementation exponent, low-frequency formation resistivity, the clay volume fraction, Qv, and a bound water volume.

10. The method of claim 1, comprising determining the multi-frequency dielectric measurements using a tool conveyed via Wireline.

11. The method of claim 1, comprising determining the multi-frequency dielectric measurements using a logging-while-drilling or measurement-while-drilling tool.

12. The method of claim 1, comprising determining the multi-frequency dielectric measurements on a core or a cutting sample from a wellsite.

13. The method of claim 1, comprising determining the multi-frequency dielectric measurements at the plurality of frequencies, wherein the plurality of frequencies is larger than $D/a^2$ where D is the diffusion coefficient of cations of the brine in the formation and a is a size of a particle of clay in the formation.

14. A method of determining a Cation Exchange Capacity (CEC) of a formation, the method comprising:
measuring multi-frequency dielectric measurements from the formation, wherein the multi-frequency dielectric measurements comprise dielectric measurements measured from the formation at a plurality of frequencies;
using a dielectric dispersion model including both one or more geometric effects and one or more electrochemical effects of the formation and clay in the formation over the plurality of frequencies, wherein the one or more geometric effects comprises a fraction of one or more cations in a Stern layer, and wherein the one or more electrochemical effects include an apparent conductivity of one or more clay particles in the formation;
inverting the multi-frequency dielectric measurements along with one or more additional formation characteristics with the dielectric dispersion model to output the CEC of the formation; and
applying the CEC to resistivity logging data; and
based on the resistivity logging data, determining an hydrocarbon content in the formation.

15. The method of claim 14, wherein the dielectric dispersion model for shaly sands assumes the formation comprises spherical, non-charged rock grains and spheroidal, charged clay grains with a fixed aspect ratio.

16. The method of claim 14, wherein the dielectric dispersion model for clay-containing formations comprises:
calculating a dielectric response of a non-clay mineral phase and free water; and
mixing a portion of the clay coated by bound water and surrounded by a double layer into a background phase.

17. The method of claim 14, wherein the one or more additional formation characteristics comprise rock matrix permittivity, a temperature of the formation, a pressure of the formation, textural parameters of rock in the formation, total porosity of the rock in the formation, permittivity of hydrocarbon in the formation, volume fraction of the clay in the formation, and combinations thereof.

18. The method of claim 17, comprising further outputting one or more of water-filled porosity, water salinity, an aspect ratio of one or more clay particles, a formation cementation exponent, a clay volume fraction, a low-frequency formation resistivity, a size of the clay in the formation, water saturation, Qv, and combinations thereof.

19. A non-transitory computer-readable medium storing computer-executable instructions, that when executed by at least one processor, causes the at least one processor to perform the following:
inputting multi-frequency dielectric measurements into a dielectric dispersion model, wherein the multi-frequency dielectric measurements comprise dielectric measurements obtained from a formation at a range of multiple frequencies, and wherein the dielectric dispersion model is based on one or more geometric effects and one or more electrochemical effects of the formation and clay in the formation over the range of multiple frequencies, wherein the one or more geometric effects comprises a fraction of one or more cations in a Stern layer, and wherein the one or more electrochemical effects include an apparent conductivity of one or more clay particles in the formation;
inverting the multi-frequency dielectric measurements with the dielectric dispersion model to output a Cation Exchange Capacity (CEC) of the formation; and
applying the CEC to resistivity logging data; and
based on the resistivity logging data, determining an hydrocarbon content in the formation.

20. The non-transitory computer-readable medium of claim 19, wherein the computer-executable instructions further cause the at least one processor to select a dielectric dispersion model based on one or more properties of the formation.

21. The non-transitory computer-readable medium of claim 19, wherein the computer-executable instructions further cause the at least one processor to:
assume the formation comprises spherical, non-charged rock grains and spheroidal, charged clay grains with a fixed aspect ratio, when the formation is determined to substantially comprise shaly sand; and
calculate a dielectric response of a non-clay mineral phase and free water and mix the clay coated by bound water and surrounded by a double layer into a background phase.

22. The method of claim 1, wherein at least one of the determination of the CEC, the characteristic related to a shape of the clay and the hydrocarbon content is performed in real-time.

* * * * *